United States Patent [19]
Nacamuli et al.

[11] Patent Number: 5,952,536
[45] Date of Patent: Sep. 14, 1999

[54] AROMATICS AND TOLUENE/TRIMETHYLBENZENE GAS PHASE TRANSALKYLATION PROCESSES

[75] Inventors: Gerald J. Nacamuli, Mill Valley; Roger F. Vogel, Fairfield; Stacey I. Zones, San Francisco, all of Calif.

[73] Assignee: Chevron Chemical Co. LLC, San Francisco, Calif.

[21] Appl. No.: 09/054,378

[22] Filed: Apr. 2, 1998

[51] Int. Cl.$^6$ .................................................. C07C 5/22
[52] U.S. Cl. .......................................... 585/475; 585/474
[58] Field of Search ................... 585/475, 474; 208/137, 238

[56] References Cited

U.S. PATENT DOCUMENTS

| | | | |
|---|---|---|---|
| Re. 31,781 | 12/1984 | Dwyer | 585/481 |
| 4,083,886 | 4/1978 | Michalko | 210/672 T |
| 4,264,473 | 4/1981 | Tu et al. | 252/432 |
| 4,341,914 | 7/1982 | Berger | 585/474 |
| 4,723,048 | 2/1988 | Dufresne et al. | 585/474 |
| 4,910,006 | 3/1990 | Zones et al. | 423/328 |
| 5,030,787 | 7/1991 | Absil et al. | 595/475 |
| 5,120,425 | 6/1992 | Zones et al. | 208/46 |
| 5,178,748 | 1/1993 | Casei et al. | 208/46 |
| 5,254,514 | 10/1993 | Nakagawa | 502/62 |
| 5,391,287 | 2/1995 | Nakagawa | 208/46 |
| 5,406,016 | 4/1995 | Cook et al. | 585/475 |
| 5,441,721 | 8/1995 | Valyocsik | 423/706 |
| 5,475,180 | 12/1995 | Shamshoum et al. | 585/475 |
| 5,512,267 | 4/1996 | Davis et al. | 423/705 |
| 5,569,805 | 10/1996 | Beck et al. | 585/446 |
| 5,580,540 | 12/1996 | Nakagawa | 423/718 |
| 5,653,956 | 8/1997 | Zones | 423/706 |

FOREIGN PATENT DOCUMENTS 825 151 A1 of 0000 European Pat. Off. .

OTHER PUBLICATIONS

Dumitriu et al "Transalkylation of the Alkylation Hydrocarbon in the Presence of Ultrastable Y Zeolites", 1996.

Jeanneret "UOP Tatoray Process", 1997.

Wang et al., "Disproportionation of Toluene and of Trimethylbenzene and Their Transalkylation over Zeolite Beta", Ind. Eng. Chem. Res. 1990, 29, 2005–2012.

Das et al., "Transalkylation and Disproportionation of Toluene and $C_9$ Aromatics over Zeolite Beta", Catalysis Letters 23 (1994) 161–168.

Das et al., "Zeolite Beta Catalyzed $C_7$ and $C_9$ Aromatics Transformation", Applied Catalysis A: General 116(1994) 71–79.

Hulea et al., "Study of the Transalkylation of Aromatic Hydrocarbons over SAPO–5 Catalysts", Microporous Materials 8 (1997) 201–206.

Meshram et al., "Transalkylation of Toluen with $C_9$ Aromatic Hydrocarbons over ZSM5 Zeolites", J. Chem. Tech. Biotechnol. 1984, 34A, 119–126.

Wu et al., "Toluene Disproportionation and Transalkylation Reaction Over Mordenite Zeolite Catalysts", Applied Catalysis, 7 (1983) 283–194.

Bhattacharyya et al., "Transalkylation of Alkyl Aromatic on Zeolite Catalysts", Research and Industry, vol. 34, Dec. 1989, pp. 281–285.

Dumitriu et al., "Transalkylation of the Alkylaromatic Hydrocarbons in the Presence of Ultrastable Y Zeolities—Transalkylation of Toluene with Trimethylbenzene", Applied Catalysis A: General 135 (1996) 57–81.

Jeanneret, "UOP Tatoray Process", Handbook of Petroleum Refining Process, $2^{nd}$, ed., 1997.

*Primary Examiner*—Glenn Caldarola
*Assistant Examiner*—Thuan D. Dang
*Attorney, Agent, or Firm*—David M. Tuck

[57] ABSTRACT

A gas phase, aromatics transalkylation process that comprises contacting a stream containing aromatic hydrocarbons with a catalyst comprising a zeolite selected from the group consisting of SSZ-26, Al-SSZ-33, CIT-1, SSZ-35, and SSZ-44 in the presence of added hydrogen and in the gas phase, to produce transalkylated product. The aromatics stream comprises one or more aromatic hydrocarbons, one of the hydrocarbons having at least one alkyl group attached thereto, the alkyl group comprising a C1, C2, C3 or C4 hydrocarbyl group. A preferred aromatics transalkylation process comprises contacting toluene or benzene or a mixture thereof with a stream containing trimethylbenzene in the presence of added hydrogen. The catalyst preferably contains a mild hydrogenation metal, such as nickel or palladium.

23 Claims, 4 Drawing Sheets

AROMATICS AND TOLUENE/TRIMETHYLBENZENE GAS PHASE TRANSALKYLATION PROCESSES

FIELD OF THE INVENTION

The invention relates to gas phase processes for aromatics transalkylation, especially for preparing xylenes by transalkylation of toluene with trimethylbenzene (TMBZ). The invention operates in the presence of added hydrogen-and utilizes a zeolite catalyst that optionally contains a mild hydrogenation metal.

BACKGROUND OF THE INVENTION

Aromatic hydrocarbons are the building blocks for many industrially important products. They are generally produced in a petrochemicals complex which produces several aromatics. When the complex produces both benzene (BZ) and para-xylene (PX), it is often desirable to transalkylate by-product toluene (T) with trimethylbenzenes (TMBZ), which may be obtained from a C9+ aromatics stream (C9+) derived from reformate. This transalkylation helps maximize the yield of xylenes. The xylenes produced can then be converted to valuable PX by further processing.

It is known to carry out aromatics transalkylation processes using zeolites either in the gas phase, or as a mixture of gas and liquid, i.e., as a partial liquid phase process. The type of processing depends on a variety of factors, including feed, catalyst, operating temperature, etc. Unfortunately, the relationship between catalyst structure and the resultant efficacy for aromatics transalkylation, especially for any particular aromatics transalkylation reaction, such as T/TMBZ, is far from predictable. This is evidenced by the plethora of recent studies and patents on the testing and use of various zeolites for aromatics transalkylation.

Various zeolites, having different crystallographic structures, have been disclosed as catalysts for gas phase aromatics transalkylation processes, particularly for the T/TMBZ transalkylation process, also termed the T/C$_{9+}$ aromatics transalkylation process. For example, zeolite beta is taught as a catalyst in J. Das et al., "*Transalkylation and Disproportionation of Toluene and C9 Aromatics over Zeolite Beta*", Cat. Lett., 23 (1994) 161–168. See also I. Wang et al., "*Disproportionation of Toluene and of Trimethylbenzene and their Transalkylation over Zeolite Beta*", Ind. Eng. Chem. Res., 29, (1990) 2005–2012; and J. Das et al., "*Zeolite Beta Catalyzed C$_7$ and C$_9$ Aromatics Transformation*", Appl. Cat. A, Gen., 116 (1994), 71–79.

The use of SAPO-5 for gas phase T/C$_{9+}$ transalkylation is disclosed by V. Hulea et al., "*Study of the Transalkylation of Aromatic Hydrocarbons Over SAPO-5 Catalysts*", Microporous Materials, 8 (1997), pp. 201–206. Also, E. Dunitriu et al., in "*Transalkylation of the Alkylaromatic Hydrocarbons in the Presence of Ultrastable Y Zeolites, Transalkylation of Toluene with Trimethylbenzenes*", (Applied Cat. A: General 135 [1996]57–81) teaches using ultra stable Y zeolite for gas phase T/C9+ aromatics transalkylation.

Two T/C9+ transalkylation processes based on mordenite are practiced commercially. One process uses added hydrogen, the other does not. The hydrogen based process, known as the Tatoray Process®, was developed about 20 years ago and is licensed by UOP. The process that does not use hydrogen is known as the Xylenes Plus Process® and is licensed by IFP. It operates using vaporized feed reacting at low pressures in a non-hydrogen atmosphere. A non-noble metal catalyst is used in a moving bed type reactor.

In both processes, acidic mordenite is the catalyst. The Tatoray Process® operates at gas phase conditions: about 400 psig, 800–900° F., a WHSV of 1–2 hr$^{-1}$ and a H$_2$/hydrocarbon (HC) mole ratio of between 2 and 4. Under these conditions mordenite is prone to coking and is thus unstable. The Xylenes Plus Process® also operates at gas phase conditions. It is believed that the operating pressure ranges from 25–100 psig and the temperature ranges from 600–900° F. Feed to these processes is a mixture of toluene and a C9+ aromatics stream, usually a reformate distillation cut which contains propylbenzenes, trimethylbenzenes and methylethylbenzenes.

Over the years, catalyst development has improved the stability as well as the initial activity of mordenite for this process. Dufresne et al., in U.S. Pat. No. 4,723,048 added a metal from the group consisting of Ni, Pd and Group IB metals in combination with a metal selected from the Group IV metals. French Pat. App. 79-30665 discloses the use of a mordenite with a small pore size, i.e., 4.5–5.0 Å, containing nickel, palladium or silver. Another approach is to modify the zeolite, for example as disclosed in U.S. Pat. No. 4,083,886. Here a mordenite, such as H Zeolon mordenite, is treated in refluxing ammonium hydroxide solution containing 5 wt % NH$_3$ at a pH of at least 9.5 at 90° C. The resulting catalyst is claimed to have improved activity. U.S. Pat. No. 4,264,473 to Tu et al., also teaches a method of catalyst manufacture for mordenite using an ammoniacal treatment. This treated zeolite is a good catalyst for T/C9+ aromatics transalkylation. U.S. Pat. No. 4,341,914 to Berger discloses a process configuration for T/C9+ transalkylation using mordenite. Here indan, a catalyst poison, is removed from fresh C9+ aromatics feed by distillation. U.S. Pat. No. 4,083,886 to Michalko discloses transalkylation using mordenite subjected to aqueous ammoniacal treatment calcined in intimate admixture with a refractory oxide.

Also, Jung-Chung Wu et al., in "*Toluene Disproportionation and Transalkylation Reaction Over Mordenite Zeolite Catalysts*", Applied Cat. (1983) pp. 283–294, discusses mordenite catalysts containing copper and palladium. U.S. Pat. No. 5,475,180 to Shamshoum describes a toluene disproportionation process. This process uses mordenite impregnated with 1.0–1.5 wt % nickel, and a toluene feed containing 4–12.5 wt % of heavy reformate, which contains xylenes and C9 aromatics. The process increases xylene production.

Aside from beta, Y, SAPO-5 and mordenite, other zeolites have been taught for gas phase T/C9+ aromatics transalkylation. For example, Absil et al., in U.S. Pat. No. 5,030,787 teach the desirability of using zeolites having a constraint index (C.I.) of from 1 to 3 for this reaction. Disclosed zeolites include steamed beta-containing Pt and MCM-22. Absil et al., also teach that adding metals, including Ni, can improve catalyst life for some of these zeolites.

Also, U.S. Pat. No. 5,441,721 to Valyocsik discloses using zeolite MCM-58, to catalyze a wide variety of conversion processes. One specific example includes "transalkylation of aromatics, in gas or liquid phase". Also, U.S. Pat. No. 5,569,805 to Beck et al. discloses the use of materials having the structure of MCM-58 for the catalytic conversion of aromatic compounds. The gas phase transalkylation of BZ with diethylbenzene is disclosed in Examples 27–29. MCM-58 is similar to SSZ-42 as they have the same topology as indicated by their X-ray diffraction patterns.

There are also numerous U.S. patents that disclose the use of zeolites for partial liquid phase (PLP) transalkylation. By PLP, the person skilled in the art means that the reactants and/or transalkylation products are at a pressure and temperature such that they are substantially in the liquid phase. The "partial" in PLP refers to the fact that there are also gaseous by-products, for example, derived from feed dealkylation, present in the reaction zone. Thus, PLP transalkylation requires a combination of pressures (typically between 300–600 psig) and temperatures (generally below 600° F.), such that the feed and transalkylation products are substantially in the liquid phase. The catalyst typically does not contain a hydrogenation/dehydrogenation metal such as Ni or Pt. Furthermore, hydrogen, a gas, is not added in PLP transalkylation.

An example of a commercial aromatics transalkylation processes that uses PLP transalkylation conditions involves the transalkylation of benzene with diisopropylbenzene to make cumene. Patents related to this include U.S. Pat. No. 4,891,458 to Innes et al., which teaches transalkylation using zeolite beta.

Various other zeolites are known for partial liquid phase transalkylation processes; see U.S. Pat. No. 5,149,894 to Zones et al. (SSZ-25), U.S. Pat. No. 5,653,956 to Zones et al. (SSZ-42), and U.S. Pat. No. 5,254,514 to Nakagawa (SSZ-37). SSZ-37 is believed to be related to NU-87, and the use of NU-87 for transalkylation is disclosed in U.S. Pat. No. 5,178,748 to Casci et al. Also, EP 825151 A1 discloses the use of dealuminated NU-87 in the transalkylation of toluene with C9 aromatics in the presence of hydrogen.

Other patents or patent applications that disclose PLP transalkylation include those directed to the use of zeolites SSZ-26, SSZ-33, SSZ-35, SSZ-44, and CIT-1. SSZ-26 is described in U.S. Pat. No. 4,910,006; SSZ-33 and Al-SSZ-33 are described in U.S. Pat. No. 4,963,337; SSZ-35 is described in U.S. Pat. No. 5,316,753; SSZ-44 is described in U.S. Pat. No. 5,580,540 and CIT-1 is described in U.S. Pat. No. 5,512,267. These patents are all incorporated herein by reference in their entirety.

The patents covering these zeolites teach their utility for transalkylation of benzene, toluene and xylene using a transalkylating agent which is a polyalkyl aromatic hydrocarbon containing two or more alkyl groups that each may have from two to four carbon atoms. Preferred polyalkyl aromatic hydrocarbons are the dialkylbenzenes, especially diisopropylbenzene. There is no suggestion in any of the patents that these known zeolites would be useful catalysts for gas phase transalkylation in the presence of added hydrogen. Nor is there any suggestion that these zeolites would be especially effective for the gas phase T/TMBZ transalkylation process in the presence of a mild hydrogenation metal.

In the T/TMBZ transalkylation reaction, equilibrium sets the toluene and TMBZ conversion, as well as the yield of product benzene and xylene. An ideal catalyst would give an equilibrium concentration of benzene and xylenes with no light ($C_{5-}$) or heavy ($C_{10+}$) aromatics.

Depending on the reactants or desired products, some selective dealkylation may be advantageous. For example, when the feed to a T/TMBZ transalkylation process contains aromatic hydrocarbons having ethyl or propyl groups, selective dealkylation of these alkyl groups (without methyl group dealkylation) can result in an improved process. For example in T/TMBZ transalkylation, deethylation of methylethylbenzene to toluene reduces the amount of an undesirable component and produces a useful feed component.

It would be desirable to develop a T/TMBZ transalkylation process where the catalyst is more active and more stable than current commercial catalysts. It would also be advantageous if this improved catalyst has xylene and benzene yields that are close to the equilibrium yields, e.g., at least 90% of the xylene equilibrium yield and less than 120% of the benzene equilibrium yield. These improvements would result in a transalkylation process that operates at lower temperature and pressure, and has higher yields of xylenes, and lower yields of BZ (due to less feed degradation). In addition, the improved catalyst stability would lead to longer cycle lengths, so the process would have lower capital investment, lower operating costs, and higher cash flow. If the catalyst were also able to selectively dealkylate ethylated and/or propylated hydrocarbons, for example, deethylate methylethylbenzene to toluene and/or dealkylate propylbenzene to benzene, this would be especially advantageous.

There is still a need for improved catalysts and processes for gas phase aromatics transalkylation, especially for T/TMBZ transalkylation. Unfortunately, because zeolite catalysts have such a wide variety of chemical structures, one cannot yet predict how useful a particular zeolite will be for any particular transalkylation process. Nor can one predict whether to use gas phase or liquid phase transalkylation conditions. The current state of the art is such that one cannot predict how active or how selective a particular zeolite catalyst, having a unique chemical structure, will be for any particular transalkylation reaction under particular transalkylation conditions. The structure/activity relationship for zeolites in, for example the T/TMBZ transalkylation process, is still being developed.

One object of the present invention is to provide a gas phase T/TMBZ transalkylation process that has a xylene yield that is close to equilibrium. Another object of the invention is to provide an improved gas phase T/TMBZ transalkylation process wherein the catalyst has good stability and selectivity.

BREIF DESCRIPTION OF THE FIGURES

FIG. 1 is a graph comparing the catalytic activity of 5 zeolites in the transalkylation of toluene with trimethylbenzene (T/TMBZ). The wt % toluene conversion is shown as a function of temperature. The toluene conversion at equilibrium at 620° F. is calculated to be 55.3 wt %. This value is shown on this figure as a line.

SUMMARY OF THE INVENTION

Figure 1:
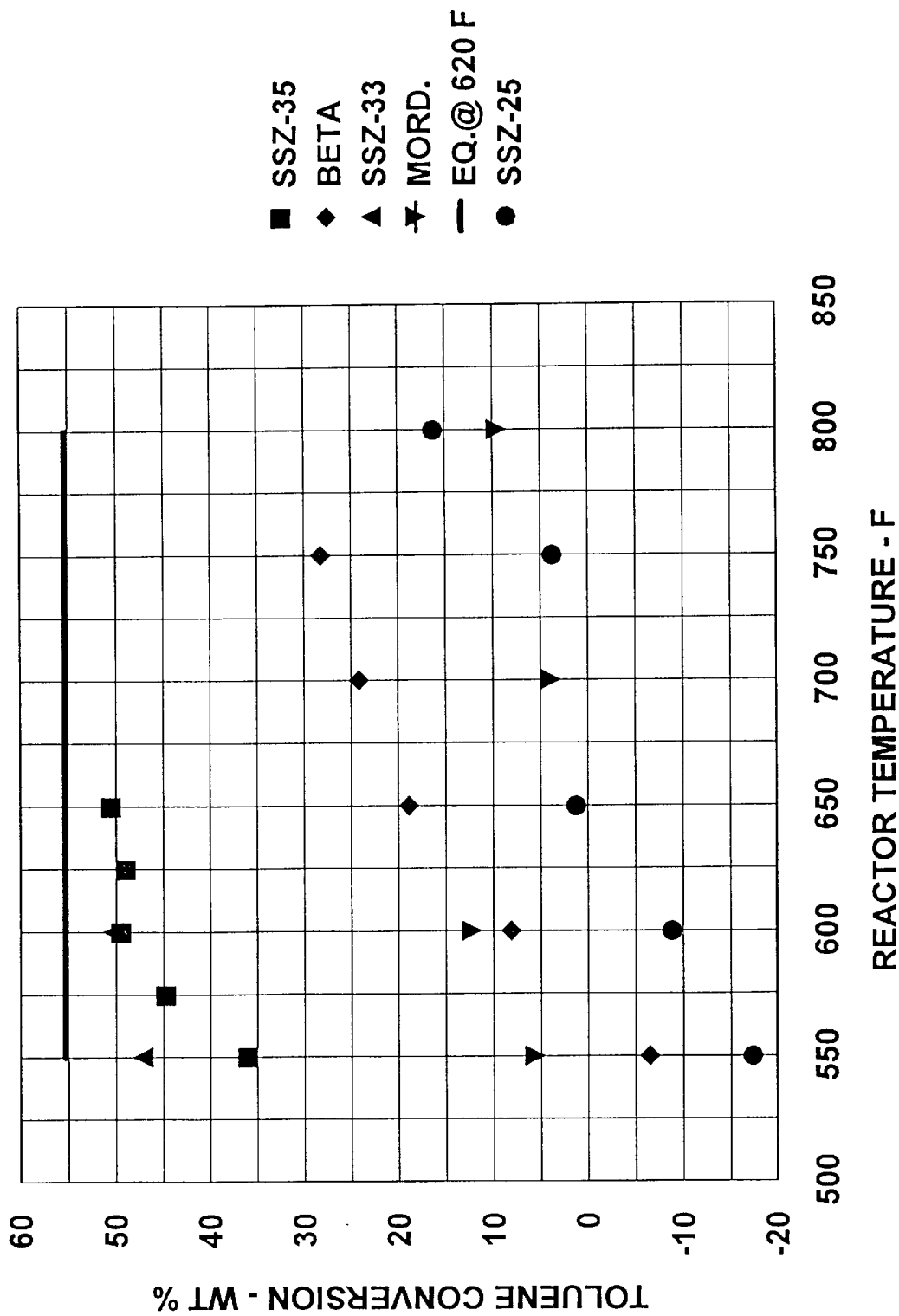

In one embodiment, the present invention is a gas phase aromatics transalkylation process, that uses a catalyst comprising a zeolite selected from the group consisting of SSZ-26, Al-SSZ-33, CIT-1, SSZ-35, and SSZ-44 and added hydrogen. In a preferred embodiment, the invention is a method of making xylenes by the gas phase transalkylation of toluene with a stream containing trimethylbenzenes (T/TMBZ transalkylation). The method comprises contacting a hydrocarbon-containing stream comprising toluene, TMBZ and added hydrogen in the gas phase with said zeolites. These zeolites are able to provide high yields of xylenes for long periods at these gas phase conditions. More prgroup consihe zeolite is selected from the group consisting of Al-SSZ-33, SSZ-35, and SSZ-44, and most preferably the zeolite is Al-SSZ-33 or SSZ-35. According to a preferred embodiment, the zeolite contains a mild hydrogenation component, such as Ni or Pd.

In one embodiment, the invention is a gas phase aromatics transalkylation process, comprising contacting a stream comprising one or more aromatic hydrocarbons with a catalyst comprising a zeolite selected from the group consisting of SSZ-26, Al-SSZ-33, CIT-1, SSZ-35, and SSZ-44 in the presence of added hydrogen and in the gas phase, to produce transalkylated product. The feed can comprise a mixture of hydrocarbons or consist essentially of a single hydrocarbon, such as toluene. In the case where a single hydrocarbon is transalkylated, the transalkylation process is disproportionation (i.e. production of benzene and xylenes from toluene).

One of the aromatic hydrocarbons in the feed must have at least one alkyl group attached thereto; the alkyl group is selected from C1, C2, C3 or C4 hydrocarbyl groups. Preferably, the aromatic hydrocarbon stream comprises one or more hydrocarbons selected from the group consisting of benzene, toluene, xylene, ethylbenzene, n-propylbenzene, isopropylbenzene, 1,2,3, trimethylbenzene, 1,2,4, trimethylbenzene, 1,3,5, trimethylbenzene, and the isomers of diethylbenzene, , diisopropylbenzene, and methylethylbenzene. More preferably, at least one of the aromatic hydrocarbons contains one, or more, methyl groups. In a preferred embodiment, the invention is a gas phase aromatics transalkylation process wherein the aromatic hydrocarbon stream comprises a mixture of toluene and TMBZ, or a mixture of benzene and TMBZ.

Among other factors, the invention is based on our discovery that zeolites selected from the group consisting of SSZ-26, Al-SSZ-33, CIT-1, SSZ-35, and SSZ44 are excellent catalysts for gas phase transalkylation of toluene with TMBZ in the presence of added hydrogen. These catalysts appear to have just the right structural properties for transalkylation reactions to occur readily. The produced xylene can be obtained in at least 80% of the equilibrium yield, and typically at 90+% of the equilibrium yield, when a synthetic test feed consisting of a T/TMBZ mixture (as described in Ex. 5) is used. Additionally, benzene yields are only slightly above equilibrium. We have also found that these catalysts have surprisingly high activity for aromatics transalkylation. This high activity allows for operation at substantially lower operating temperatures than most prior art catalysts. Moreover, the amount of by-product methane using these catalysts is low (due to low cracking and/or demethylation activity) under gas phase conditions.

As noted in the Background section, the SSZ zeolites useful in the present invention have been disclosed as transalkylation catalysts in partial liquid phase transalkylation processes. However, we have found that for aromatics transalkylation, and particularly for T/TMBZ transalkylation, the performance of these zeolites is significantly improved when used in the gas phase in the presence of added hydrogen. The performance is even better when a mild hydrogenation component is added to the zeolite. This excellent performance was unexpected in view of the art. Although these zeolites had been broadly taught to be useful for PLP transalkylation, they had not been taught as useful for gas phase transalkylation. Thus, it was assumed that PLP transalkylation conditions were to be used. And yet, the results we have obtained using these zeolites at gas phase conditions with added hydrogen for T/TMBZ transalkylation are unexpectedly good, and indeed surprisingly better than those obtained at PLP conditions.

In a preferred embodiment, the feed contains at least two aromatic hydrocarbons. One preferred aromatics transalkylation process comprises contacting benzene or toluene or a mixture thereof with a hydrocarbon stream containing TMBZ in the presence of added hydrogen and a zeolite catalyst selected from the group consisting of zeolites having the X-ray diffraction pattern of SSZ-26, Al-SSZ-33, CIT-1, SSZ-35, and SSZ-44. Preferred catalysts comprise a zeolite selected from the group consisting of Al-SSZ-33 and SSZ-35. Although not required, the catalyst preferably also contains a mild hydrogenation metal, such as nickel.

In a preferred embodiment, the invention is a process for preparing xylenes, comprising separating a whole naphtha into a light naphtha comprising C7 hydrocarbons and a heavy naphtha comprising C9+ hydrocarbons; reforming the light naphtha using a Pt L-zeolite catalyst, to produce a first reformate containing toluene; separating a toluene-rich stream from said first reformate; reforming the heavy naphtha using a non-zeolitic Group VIII reforming catalyst to produce a second reformate; separating a stream containing TMBZ from said second reformate; and transalkylating said toluene-rich stream with said TMBZ-containing stream in the gas phase in the presence of added hydrogen using a catalyst comprising a zeolite selected from the group consisting of SSZ-26, Al-SSZ-33, CIT-1, SSZ-35, and SSZ-44; and separating a xylene-rich stream. The zeolite preferably contains a mild hydrogenation component, such as nickel or palladium.

In another embodiment the invention is the gas phase disproportionation of toluene using a catalyst comprising a zeolite selected from the group consisting of SSZ-26, Al-SSZ-33, CIT-1, SSZ-35, and SSZ-44. In another embodiment the invention is a BZ/TMBZ transalkylation process to make toluene and xylenes.

DETAILED DESCRIPTION OF THE INVENTION

The present invention is directed to aromatics transalkylation processes that use a certain group of zeolites with unique properties. These zeolites are referred to herein as "SSZ-##", for example "zeolite SSZ-44" or "zeolite SSZ-26" or simply "SSZ-44" and "SSZ-26", respectively. These SSZ zeolites are defined by their X-ray diffraction patterns and are known in the art.

We have now developed improved processes for the transalkylation of aromatics, especially for the transalkylation of toluene with TMBZ. In one embodiment, the invention is a gas phase process that comprises passing toluene, a stream containing TMBZ and added hydrogen over a catalyst comprising a zeolite selected from the group consisting of SSZ-26, Al-SSZ-33, CIT-1, SSZ-35, and SSZ-44. The catalyst preferably contains a mild hydrogenation metal. Although transalkylation of toluene with TMBZ is a preferred transalkylation process and is discussed herein in detail, this particular embodiment is intended to be exemplary rather than limiting. As will be appreciated by one skilled in the art, the teachings herein are applicable to transalkylation of other aromatics hydrocarbons with other transalkylating agents.

As used herein, the term "comprising" is open-ended. It is intended to specify the presence of the stated features, integers, steps, or components but does not preclude the presence or addition of one or more other features, integers, steps or components. Although the terms "comprises" or "comprising" are generally used throughout this specification, these terms are intended to encompass both the terms "consisting essentially of", and "consisting of" in various preferred aspects and embodiments of the present invention.

As used herein, the term "trimethylbenzene" or "TMBZ" is intended to include one or more of the trimethylbenzenes: 1,2,3, trimethylbenzene; 1,2,4, trimethylbenzene; and 1,3,5, trimethylbenzene. In the art, the term "C9" or "C9+" has also been used to include the trimethylbenzene encompassed in the term "TMBZ" herein. The TMBZ is preferably a component of a hydrocarbon stream, more preferably a C9 aromatics heart-cut from reformate. This cut generally contains other C9 aromatics such as propylbenzene and methylethylbenzene (MEBZ), and some C10+ hydrocarbons.

As used herein, the term "gas phase" is intended to mean that the feed and desired aromatics products are present in the bulk phase as gases, rather than liquids. This term is synonymous with vapor phase. The phase for these hydrocarbons depends on the combination of temperature and pressure, which can be determined by a chemical engineer of ordinary skill in the art using standard methods.

As used herein, the terms "mild hydrogenation component" or "mild hydrogenation metal" are intended to include hydrogenation metals alone or in combination that, when incorporated into the zeolite, improve catalyst life. These mild hydrogenation metals do not significantly hydrogenate the aromatic ring of the aromatic hydrocarbons present in the feed or products, nor do they significantly crack the aromatics under transalkylation conditions.

The term "zeolite", as used herein, refers to a molecular sieve containing a silicate lattice, usually in association with some aluminum, boron, gallium, iron, and/or titanium. One skilled in the art will recognize that the teachings relating to zeolites are also applicable to the more general class of materials having a fixed open network structure called molecular sieves. Preferably the zeolites are obtained in their silicate, aluminosilicate, or borosilicate form. The term "silicate" refers to a zeolite having a very high mole ratio of silicon oxide relative to aluminum oxide, preferably a mole ratio greater than 400. As used herein the term "aluminosilicate" refers to a zeolite containing both alumina and silica and the term "borosilicate" refers to a zeolite containing oxides of both boron and silicon.

As used herein, the term "hydrocarbyl" is intended to include C1, C2, C3 and C4 alkyl groups including methyl, ethyl, propyl, isopropyl, butyl, isobutyl, t-butyl, cyclopropyl, and methylcyclopropyl.

The term constraint index (C.I.) as used herein is defined in J. Cat. 67, (1981) pp. 218–222. The determination of C.I. is also discussed in U.S. Pat. No. 4,481,177.

Zeolites

Zeolites useful in this invention include SSZ-26, Al-SSZ-33, SSZ-35, SSZ-44 and CIT-1.

The preparation and properties of SSZ-26 are described in U.S. Pat. No. 4,910,006 to Zones et al.; the x-ray diffraction pattern for this zeolite is shown in Table A.

The preparation and properties of Al-SSZ-33 are described in U.S. Pat. No. 4,963,337 to Zones et al.; the x-ray diffraction pattern for this zeolite is shown in Table B. The SSZ-33 structure consists of a 12-membered ring pore opening with a three dimensional pore structure; the larger pore opening is 6.4×7 Å. A recent article (*J Cat.*, 1997, 167,438–446), indicates that SSZ-33 consists of 12- and 10-membered ring pore openings. SSZ-33 has channels in the x, y, and z directions that interconnect. Also, the 12 and 10-membered ring channels interconnect.

As synthesized, Zeolite SSZ-33 is a borosilicate. This borosilicate is substantially inactive in gas phase aromatics transalkylation processes. However, the boron can be substituted with other elements to produce active transalkylation catalysts. As described in the '337 patent, boron can be replaced with aluminum to produce what we call "Al-SSZ-33" herein. The aluminum preferably replaces at least 50% of the initial boron, preferably, at least 75% and more preferably 90% or more of the boron initially present.

TABLE A

Calcined SSZ-26

| 2θ | d/n | I/Io X 100 |
|---|---|---|
| 7.78 | 11.3 | 100 |
| 20.22 | 4.392 | 18 |
| 21.34 | 4.164 | 5 |
| 21.98 | 4.044 | 15 |
| 22.93 | 3.878 | 13 |
| 23.08 | 3.853 | 19 |
| 26.48 | 3.366 | 12 |

TABLE B

Calcined SSZ-33

| 2θ | d/n | I/Io X 100 |
|---|---|---|
| 7.81 | 11.32 | 100 |
| 20.43 | 4.347 | 46 |
| 21.44 | 4.144 | 9 |
| 22.02 | 4.037 | 41 |
| 22.18 | 3.837 | 28 |
| 26.80 | 3.326 | 31 |

The preparation and properties of SSZ-35 are described in U.S. Pat. No. 5,316,753 to Nakagawa; the x-ray diffraction pattern for this zeolite is shown in Table C: SSZ-35 has a 10-ring pore structure. The pore diameter is 5.8 Å. It consists of a one-dimensional channel system, perodically opening into larger cavities.

TABLE C

Calcined SSZ-35

| 2θ | d/n | I/Io X 100 |
|---|---|---|
| 8.00 | 11.04 | 100 |
| 9.67 | 9.14 | 15.5 |
| 15.42 | 5.74 | 1.5 |
| 19.01 | 4.67 | 7.9 |
| 19.44 | 4.56 | 12.0 |
| 19.48 | 4.55 | 12.5 |
| 19.92 | 4.45 | 7.0 |
| 21.70 | 4.09 | 3.2 |
| 22.84 | 3.89 | 5.0 |
| 24.81 | 3.59 | 6.7 |
| 27.50 | 3.24 | 4.8 |
| 29.41 | 3.04 | 3.9 |

The preparation and properties of SSZ-44 are described in U.S. Pat. No. 5,580,540 to Nakagawa; the x-ray diffraction pattern for this zeolite is shown in Table E. The pore diameter is 5.6 Å.

The preparation and properties of CIT-1 are described in U.S. Pat. No. 5,512,267 to Davis et al. The x-ray diffraction pattern for this zeolite is shown in Table F. The structures of CIT-1, SSZ-33, and SSZ-26 are similar.

TABLE F

Calcined CIT-1

| 2 Theta | D/(Å) | Intensity[1] |
|---|---|---|
| 7.7 | 11.5 | VS |
| 7.8 | 11.3 | VS |
| 9.1 | 9.75 | M |
| 12.0 | 7.38 | W |
| 13.8 | 6.39 | W |
| 14.6 | 6.06 | W |
| 15.3 | 5.77 | W |
| 17.3 | 5.11 | M |
| 18.2 | 4.86 | W |
| 19.8 | 4.48 | M-W |
| 20.5 | 4.33 | S |
| 21.5 | 4.13 | W |
| 22.1 | 4.02 | S |
| 23.0 | 3.87 | S |
| 24.1 | 3.69 | W |
| 24.4 | 3.64 | W |
| 24.8 | 3.59 | W |
| 26.8 | 3.32 | M |
| 27.9 | 3.19 | W |
| 28.4 | 3.14 | W-M |
| 29.0 | 3.08 | W |

TABLE E

Calcined SSZ-44

| 2 Theta | d | Relative Intensity |
|---|---|---|
| 7.7 | 11.4 | M-S |
| 8.0 | 11.0 | VS |
| 8.7 | 10.2 | S-VS |
| 16.0 | 5.5 | W |
| 19.2 | 4.6 | M |
| 19.6 | 4.5 | W |
| 20.5 | 4.3 | W |
| 21.6 | 4.1 | W |
| 23.8 | 3.7 | W |
| 25.6 | 3.5 | W |

The above-described zeolites are defined by their X-ray diffraction patterns. Calcination can result in changes in the intensities of the peaks as compared to patterns of the "as-synthesized" material, as well as minor shifts in the diffraction pattern. Also, the zeolite produced by exchanging the metal or other cations present in the zeolite with various other cations (such as $H^{3O}$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Preferred zeolites useful in this invention have a constraint index (C.I.) of 1 or less, more preferably between 0.20 and 0.99. It is preferred that the catalysts are comprised of small crystals and have some acidity. Preferably, the silica to alumina ratio is below about 100.

It is contemplated that other elements, such as gallium, boron and iron, can be variably substituted, at least in part, for aluminum in the zeolites. Similarly, elements such as germanium and phosphorus can be variably substituted for silicon.

The cation in these zeolites is typically sodium from the original synthesis but may also be a metal ion added using ion exchange techniques. Suitable metal ions include those from Groups IA, IIA or IIIA of the Periodic Table or a transition metal. Examples of such ions include ions of lithium, potassium, calcium, magnesium, barium, lanthanum, cerium, nickel, platinum, palladium, and the like. Typical replacing cations can also include metal cations of the rare earth and Group VIII metals, as well as mixtures of metals. Of the replacing metallic cations, cations of metals such as rare earth metals Mn, Ca, Mg, Zn, Cd, Pt, Pd, Ni, Co, Ti, Al, Sn, and Fe are particularly preferred. The zeolite can also be impregnated with the metals, or the metals can be physically and intimately admixed with the zeolite using standard methods known to the art. Preferred replacing cations include metal ions, hydrogen ions, hydrogen precursors, e.g., ammonium ions, and mixtures thereof. Particularly preferred cations are those which tailor the catalytic activity for transalkylation/disproportionation. These include hydrogen, rare earth metals and metals of Groups IIA, IIIA, IVA, IB, IIB, IIIB, IVB and VIII of the Periodic Table of the Elements.

For high catalytic activity, the zeolite should be predominantly in its hydrogen ion form. Generally, the zeolite is converted to its hydrogen form by ammonium exchange followed by calcination. If the zeolite is synthesized with a high enough ratio of organonitrogen cation to sodium ion, calcination alone may be sufficient. It is preferred that, after calcination, hydrogen ions and/or rare earth ions occupy a major portion of the cation sites. It is especially preferred that at least 80% of the cation sites are occupied by hydrogen ions and/or rare earth ions. It is envisioned that an ammoniacal treatment, such as described in U.S. Pat. No. 4,083,886, could also be used to modify these zeolites.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249, 3,140,251 and 3,140,253—all to Plank, et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in gas phase transalkylation processes.

The pure zeolite may be used as a catalyst, but generally it is preferred to mix the zeolite powder with an inorganic oxide binder such as alumina, silica, silica/alumina, or naturally occurring clays and to form the mixture into tablets or extrudates. The SSZ zeolite is preferably composited with other materials resistant to the temperatures and process conditions employed in transalkylation. Such matrix materials include active and inactive materials and synthetic or naturally occurring zeolites, as well as inorganic materials such as clays, silica and metal oxides. The final catalyst may contain from 1 to 99 wt % zeolite. Usually the zeolite content will range from 10 to 90 wt %, and more typically from 50 to 80 wt %. A preferred inorganic binder is alumina.

The SSZ zeolites useful in this invention can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the zeolite can be extruded before drying, or, dried or partially dried and then extruded. Forming tablets or extrudates is well known in the art. The extrudates or tablets will usually be cylindrical in shape. Other shapes with enhanced surface-to-volume ratios, such as fluted or poly-lobed cylinders, can be employed to enhance mass transfer rates and thus catalytic activity.

Mild Hydrogenation Metals

In a preferred embodiment, the zeolites useful in this invention contain a hydrogenation metal, preferably a mild hydrogenation metal. A mild hydrogenation metal reduces coking without substantial feed hydrogenation and subsequent cracking. It does not produce excess demethylation, nor result in extensive aromatics hydrogenation and cracking.

The zeolite can be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed.

Preferred mild hydrogenation metals comprise the Group VIII metals including Ni, Pd, Co, Fe, Ru and Rh, or a combination thereof. More preferably the metals include Ni, Pd, Co and Fe, or a combination thereof. Most preferably the metal is selected from among Ni and Pd.. The metal can be added to the zeolite by any of the methods known in the art, e.g., by ion exchange or preferably by impregnation. It is preferred that the metal be distributed uniformly throughout the zeolites. We have found that adding small amounts of a hydrogenation metal, such as Ni and Pd, improves catalyst stability and life, probably by preventing coke laydown.

Other useful metals include silver, copper, and lead, especially in combination with another metal, such as a Group VIII metal.

An effective amount of mild hydrogenation metal is added so that the rate of catalyst fouling (relative to the catalyst of hydrogenation metal) is reduced, while aromatic ring hydrogenation and hydrocarbon cracking due to the added metal are minimized. The amount of added metal depends on the particular metal, the aromatic hydrocarbons being processed and transalkylation processing conditions. This amount can be readily determined by one skilled in the art. Generally, the amount of the mild hydrogenation metal added is between 0.01 and 5.0 wt %, preferably between 0.02 and 3 wt %, and usually between 0.05 and 2.0 wt %. For example, the amount of nickel added is preferably between 0.1 to 5.0 wt %; more preferably it is between about 0.2 to 3.0 wt %, and most preferably between about 0.5 to 2.0 wt %. The amount of Pd added is preferably between 0.01 to 2.0 wt %; more preferably it is between 0.05 and 1.0 wt %. For Pt we discovered that when added to Al-SSZ-33, even 0.1 wt % platinum, it gave a catalyst that resulted in excessive hydrogenation of the aromatics followed by cracking. Pt in this instance was not a mild hydrogenation component.

Hydrocarbons and Hydrogen

Examples of suitable aromatic hydrocarbons that can be transalkylated by the gas phase process of this invention include benzene, toluene and xylene. Mixtures of aromatic hydrocarbons may also be employed. In one embodiment, the aromatic hydrocarbon that is transalkylated by the process of the invention comprises toluene, for example, a mixture of toluene with benzene, and/or xylene. In a preferred embodiment, the aromatic hydrocarbon comprises a toluene stream, more preferably a stream containing at least 90 wt % toluene, such as one containing at least 95 wt % toluene and more preferably one containing 99 wt % toluene or more. In another embodiment, the aromatic hydrocarbon comprises a benzene stream, such as a C6 reformate distillation cut, which preferably contains at least 90 wt % BZ, more preferably it contains at least 95 wt % BZ and most preferably 99 wt % BZ or more.

The transalkylating agent is preferably an aromatic hydrocarbon containing one or more alkyl groups. Each alkyl group can independently be a hydrocarbyl groups containing 1, 2, 3 or 4 carbon atoms. For example, suitable transalkylating agents include mono-, di-, tri- and tetra-alkyl aromatic hydrocarbons, such as toluene, xylene, ethylbenzene, n-propylbenzene, idiethylbenzene, methylethylbenus isomers of diethylbenzene, methylethylbenzenes (also known as ethyltoluene), trimethylbenzene, triethylbenzene, methyldiethylbenzene (diethyltoluene), di-isopropylbenzene, di-isopropyltoluene, dibutylbenzene, and the like. In one preferred embodiment of the invention, the tranalkylating agent comprises trimethylbenzene. Also, the feed can consist essentially of a single hydrocarbon, such as toluene. In this case, the transalkylation is a disproportionation reaction that produces benzene and xylenes.

As noted earlier, TMBZ includes one or more of the trimethylbenzenes, i.e., 1,2,4 trimethylbenzene; 1,3,5 trimethylbenzene; and 1,2,3 trimethylbenzene. A preferred transalkylating agent is, or is derived from, a C9+ aromatics reformate cut, e.g., a C9 reformate distillation heart-cut. Other polyalkyl aromatic hydrocarbons that may be present in this heart-cut include di-, tri- and tetra-alkyl aromatic hydrocarbons, such as the isomers of methylethylbenzene, tetramethylbenzene, ethyldimethylbenzene and the like. A distillation heart-cut containing at least 10 wt %, preferably about 15–20%. TMBZ or more is an especially preferred transalkylating agent. Preferably the reformate distillation heart-cut contains less than 15 wt %, more preferably less than 10 wt %, and most preferably less than 5 wt % of C10+ hydrocarbons. C10+ hydrocarbons can rapidly foul the catalyst. In the T/TMBZ transalkylation process of the invention, it is preferred that the transalkylated product contains a mixture of xylenes that are at or near equilibrium, and that the C8 product contains less than 5 wt % ethylbenzene, preferably less than 4 wt %, and most preferably less than 3 wt % ethylbenzene.

In one embodiment, the invention is a gas phase transalkylation process where toluene is transalkylated with TMBZ. In another embodiment, the invention is a gas phase transalkylation process where benzene is transalkylated with TMBZ. In yet another embodiment, the invention is a gas phase toluene disproportionation process, which produces benzene and xylenes.

The molar ratio of aromatic hydrocarbon to transalkylating agent will generally range from about 0.5:1 to 50:1, and preferably from about 1:1 to about 20:1, more preferably from about 1.5:1 to about 10:1, and most preferably from about 2:1 to about 4:1. Thus, for T/IMBZ transalkylation, the molar ratio of toluene to C9+ aromatics in the feed to the catalyst can range from about 0.5:1 to about 50:1, preferably the ratio is from about 1:1 to about 20:1, more preferably from about 1.5:1 to about 10:1, and most preferably from about 2:1 to about 4:1.

The added hydrogen is preferably pure hydrogen, although hydrogen containing some (e.g., 5–10%) hydrocarbons, such as methane, may be used. The hydrogen to hydrocarbon (HC) mole ratio can vary. It is preferably between 1:1 and 10:1, more preferably between 2:1 and 5:1.

Catalyst testing for T/TMBZ transalkylation using commercial feeds is complex, as the variety of products and reactions complicates the analysis of selectivity and kinetics. Therefore, catalysts can often be better assessed using a synthetic feed and screening conditions. Our synthetic feed is a mixture containing about 60 wt % toluene and about 40 wt % TMBZ; see Example 1A, below. Useful catalysts for the T/TMBZ transalkylation process—when using this synthetic feed—produce an effluent having a xylene to benzene ratio greater than 5, and an approach to xylene equilibrium that is at least 80%, preferably at least 90%, of theoretical. Test conditions are selected so that they approximate conditions of a commercial unit, i.e., 200 psig, 3:1 H2/HC, 2.4 WHSV, and temperatures starting at 500° F. Initial testing seeks to approach equilibrium toluene conversions.

One advantage of the process of the invention is that, for T/TMBZ transalkylation, the produced xylenes are at equilibrium and contain low concentrations of ethylbenzene (EB), preferably below 5 wt %, more preferably 1 wt %. EB is an inert in PX processing and must be converted in the xylene isomerization plant to light and heavy aromatics, which are then removed by distillation. A xylene stream that is low in EB allows for a reduction in the severity of operation of the xylene isomerization plant, namely a lower operating temperature, and results in lower xylene losses and a lower catalyst deactivation rate. Thus a further benefit of the invention is lower xylene losses and a longer catalyst life for the xylene isomerization plant catalyst.

Reactors and Operating Conditions

Various types of reactors and reactor configurations can be used in the gas phase aromatics transalkylation processes of this invention. For example, the process can be carried out in batchwise fashion by adding the catalyst and aromatic feedstock to a stirred autoclave, heating to reaction temperature, and then slowly adding the transalkylation agent. A heat transfer fluid can be circulated through the jacket of the autoclave, or a condenser can be provided to remove the heat of reaction and maintain a constant temperature. Large scale industrial processes may employ a fixed bed reactor operating in an upflow or downflow mode or a moving bed reactor operating with concurrent or countercurrent catalyst and hydrocarbon flows. These reactors may contain a single catalyst bed or multiple beds and may allow interstage addition of aromatics and/or interstage cooling. Interstage toluene addition and/or the interstage addition of TMBZ and interstage cooling result in more nearly isothermal operation; this enhances product quality and catalyst life. A moving bed reactor makes possible the continuous removal of spent catalyst for regeneration and replacement by fresh or regenerated catalysts.

The gas phase operating conditions useful in this invention require a combination of pressures and temperatures such that the feed and products are all in the gas phase. Preferred gas phase operating conditions include: a pressure of 100–500 psig, preferably 200 to 400 psig; a weight hour space velocity (WHSV) of between 0.5–10 $hr^{-1}$, more preferably between 1.5 and 4.0 $hr^{-1}$ and a reaction temperature of 500–900° F., more preferably between 550° F. and 800° F. and a $H_2$/HC feed mole ratio of between 1 and 10, and more preferably between 2 and 5.

For T/TMBZ transalkylation, it is preferred that the process of th invention gives high toluene and TMBZ conversions and reaction of these components produces xylenes. Especially useful catalysts have high deethylation and depropylation activities. Under operating conditions they can convert MEBZ and propylbenzene to toluene. The produced toluene can then participate in the T/TMBZ transalkylation.

Figure 4:
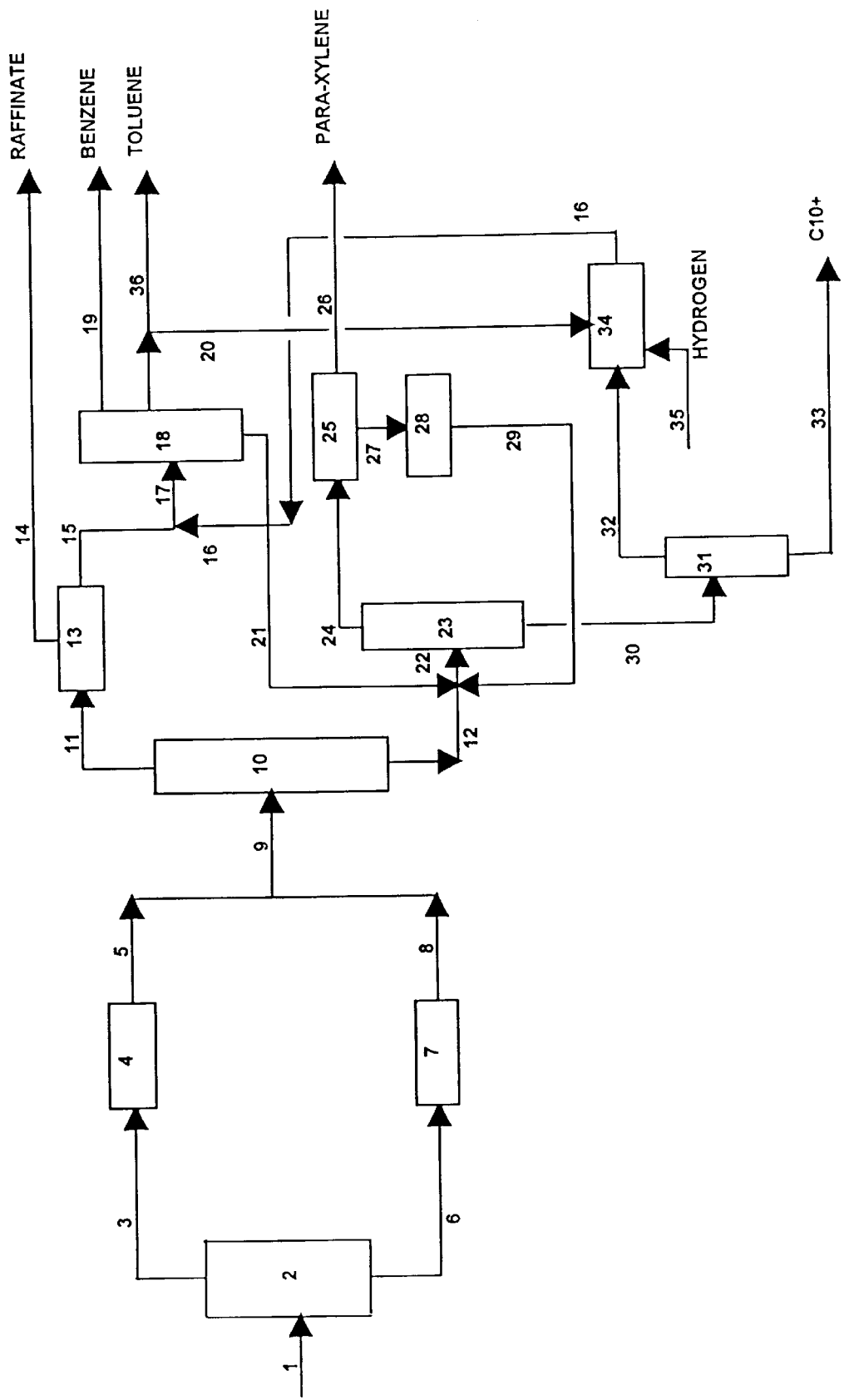
FIG. 4 is a process flow diagram showing a portion of a petrochemicals complex, which includes a T/TMBZ transalkylation unit.

FIG. 4 is a simplified Process Flow Diagram showing a preferred flow scheme for use with the present invention in an aromatics complex for maximum PX production. It includes the T/TMBZ transalkylation process as an integral part of the overall PX production scheme. A naphtha stream (1), which has been depentanized and hydrotreated to remove sulfur and nitrogen, is fed to the naphtha splitter (2). The light naphtha overhead cut (3) contains hydrocarbons whose boiling point is equal to or lower than C7 (a $C_{7-}$ cut); the heavy naphtha bottoms cut (6) contains $C_8$+ hydrocarbons, including TMBZ precursors.

The overhead (3) from the Naphtha Splitter is processed in a first reformer, such as an L-zeolite Aromatization Unit (4), to produce a first reformate containing benzene and toluene. Feed contacting the L-zeolite catalyst preferably contains less than 50 ppb sulfur. The bottoms (6) from the Naphtha Splitter is processed in a second reformer, such as in a conventional catalytic reformer (7). This reformer may use a non-zeolitic Group VIII reforming catalyst, such as chlorided $Pt/Al_2O_3$ or Pt/Sn on $Al_2O_3$ or Pt/Re on $Al_2O_3$. This scheme maximizes production of $C_6$ and $C_7$ aromatics in Unit (4), and $C_8$ and $C_9$ aromatics in Unit (7). Stream (5) and Stream (8) are combined into Stream (9) and sent to the Reformate Splitter (10). Benzene, toluene and unconverted paraffins and naphthenes in the benzene/toluene boiling range are taken overhead as Stream (11), and $C_8$, $C_9$ and $C_{10}$ aromatics are taken as bottoms cut, Stream (12).

Stream (11) is then processed in an (AEU) Aromatics Extraction Unit (13) to separate paraffins from aromatics. A variety of extraction units are commercially available and can be used. These include those licensed as UDEX, Sulfolane, and Krupp Units. The effluent from the Extraction Unit comprises a paraffin-rich raffinate, Stream (14), and an aromatics-rich stream, BZ/T Stream (15). Stream (15) is combined with Stream (16), and the resulting Stream (17) is sent to Separation Unit (18). Stream (16) is the stabilized effluent (i.e., with light ends removed) from the T/TMBZ Transalkylation Unit (34), and contains $C_6$, $C_7$, $C_8$, $C_9$ and $C_{10}$ aromatics. Separation Unit (18), provides benzene (Stream 19), a toluene-rich stream, Stream (20) and (36), and a $C_8$–$C_{10}$ aromatics stream (Stream 21) by distillation. Toluene, Stream (20), is sent to T/TMBZ Transalkylation Unit (34). Stream (36) can also be sent to Unit (34), or to gasoline blending, or for further processing, e.g., a Selective Toluene Disproportionation Unit.

Stream (21) combines with Stream (12) and Stream (29); the resulting Stream (22) is sent to the Xylene Splitter (23). Stream (29) is the stabilized effluent from the Xylene Isomerization Unit (28). The Xylene Splitter recovers xylenes as a high purity overhead cut, Stream (24). The bottoms cut from Unit (23) is Stream (30), which consists essentially of $C_9$ and $C_{10}$ aromatics. Stream (24) is sent to the PX Recovery Unit (25) where high purity PX (26) is produced. Stream 27, which contains ethylbenzene (EB) and is lean in PX but rich in ortho- and meta-xylene, is sent to the Xylene Isomerization Unit (28). The EB may be hydrodealkylated to benzene, or converted to xylenes. The stabilized effluent, Stream (29), from the Xylene Isomerization Unit (28), after B/T removal, contains $C_8$, $C_9$ and $C_{10}$ aromatics and is sent to Xylene Splitter (23) for recovery of xylenes. The bottoms cut from Unit (23), Stream (30), consisting of $C_9$ and $C_{10}$ aromatics is further processed in $C_9$/$C_{10}$ Aromatics Splitter (31) to produce a TMBZ-rich overhead cut, Stream (32), which contains primarily $C_9$ aromatics, and a $C_{10+}$ aromatics bottoms cut, Stream (33).

The TMBZ-rich Stream (32) and toluene, Stream (20), are sent to the T/TMBZ Transalkylation Unit (34) where, after partial conversion of toluene and the $C_9$ aromatics, an equilibrium mixture of xylenes is produced. Hydrogen, Stream (35), is added to Unit (34). The stabilized effluent Stream (16) from Unit (34) containing unconverted toluene and $C_9$ aromatics, and the products of the transalkylation reaction, namely, BZ, EB, xylenes, and $C_{10+}$ aromatics are sent to Unit (18) for recovery of BZ, T and $C_{8+}$ aromatics and ultimately $C_9$ aromatics. The recovered unconverted T and $C_9$ aromatics are combined with fresh toluene and $C_9$ aromatics and recycled to the T/TMBZ Transalkylation Unit (34).

Since the transalkylation process operates with excess hydrogen and a small amount of hydrogen is consumed, fresh make-up hydrogen, Stream (35), is supplied to the transalkylation reactor. The reactor effluent, which includes light ends formed during the reaction, is first cooled and then sent to a vapor-liquid separator where the light ends including excess hydrogen are recovered as a gas stream. This gas stream, which is rich in hydrogen, also contains by-product methane, ethane and propane. Most of it is recycled to the reactor inlet along with fresh make-up hydrogen, although some is excessed to prevent by-product buildup. The liquid effluent is sent to a distillation section where BZ, unconverted T, xylenes, and unconverted TMBZ along with other $C_9$ aromatics present in the feed are recovered. The $C_{10+}$ bottoms from the last distillation column (Unit 31) are usually sent to gasoline blending. Unconverted toluene and the cut containing unconverted TMBZ and other $C_9$ aromatics are combined with fresh toluene, fresh C9+ aromatics and recycle hydrogen, and sent to the transalkylation reactor.

EXAMPLES

To obtain a more complete understanding of the present invention, the following examples illustrating certain aspects of the invention are set forth. It should be understood, however, that the invention is not intended to be limited in any way to the specific details of the examples.

Example 1—Preparation of Zeolites

Ex. 1A—SSZ-26 was prepared according to U.S. Pat. No. 4,910,006, Ex. 4.

Ex. 1B—Al-SSZ-33, was prepared according to U.S. Pat. No. 4,963,337, Ex 9. The silica to alumina ratio was about 40.

Ex. 1C—SSZ-35, was prepared according to U.S. Pat. No. 5,316,753, Ex 12. The silica to alumina ratio was about 30.

Ex. 1D—CIT-1 was prepared according to U.S. Pat. No. 5,512,267, Ex 7.

Ex. 1E—SSZ-44 was prepared according to U.S. Pat. No. 5,580,540, Ex 2 and then was ion-exchanged following the proceedures of Ex. 13. The silica to alumina ratio was about 75.

In most of the examples below, the zeolite powders were formed into pellets using a die and hydraulic press (10,000 psig for 1 min). The pellets were chipped and sized to −20+40 mesh US Standard sieve size. The chips were dried at 120° C. and cooled in a desiccator.

Ex 2—Preparation of Ni/Al-SSZ-33 Catalyst

Al-SSZ-33 from Ex. 1B was formed into pellets. 3.5 g of the dry chips were calcined at 1000° F. in a muffle furnace for 4 hr to yield 3.3 g of calcined chips. Of this material, 3.05 g were used as support for the nickel oxide. 0.153 g of $Ni(NO_3)_2.6 H_2O$ from Baker (Phillipsburg, N.J., product number 2784-1) were dissolved into 4 ml of deionized water. This solution was used to impregnate the zeolite chips using the incipient wetness impregnation method. The resulting solid was placed into a circulating air oven at 120° C. for 5 hr. Following this, it was calcined in a muffle furnace by ramping to 1000° F. over 2 hr, and holding for 5 hr, then cooling in a desiccator before weighing. The finished catalyst weighed 3.07 g and contained 1 wt % Ni supported on Al-SSZ-33.

Nickel can be added to the other zeolite catalysts in the same manner.

Ex. 3—Preparation of Pd/Al-SSZ-33 Catalyst

Al-SSZ-33 from Ex 1B was formed into pellets using a die and hydraulic press. 3.7 g of the dry chips were calcined at 1000° F. in a muffle furnace for 3 hr to yield 3.4 g of calcined chips. $(NH_3)_4Pd(NO_3)_2$ (assay 35.50% Pd), 0.0096 g, from Johnson Matthey (Malvern, Pa.) was dissolved into 4.5 ml of deionized water. This solution was used to impregnate the zeolite chips using the incipient wetness impregnation method. The resulting material was placed into a circulating air oven at 20° C. for 1 hr, then heated to 60° C. for 2 hr, then dried for 16 hr at 120° C. Following this, it was calcined in a muffle furnace by ramping to 300° F. over 1 hr, holding for 1 hr, ramping to 950° F. over 1 hr, holding for 2 hr, then cooling in a desiccator before weighing. The finished catalyst weighed 3.4 g and contained 0.1 wt % Pd supported on the Al-SSZ-33.

Palladium can be added to the other zeolites in the same manner.

Comparative Ex. 4—Preparation of Pt/Al-SSZ-33 Catalyst

Zeolite Al-SSZ-33 powder (6.7 g) from Ex 1B was calcined for 3 hr at 1000° F. in a muffle furnace as described above. After cooling in a desiccator, the sample weighed 5.8 g. $Pt(NH_3)_4Cl_2$ hydrate (assay 56.3% Pt), 0.0120 g, from Johnson Matthey Co., (Malvern, Pa.) was dissolved in 30 ml of deionized water. The zeolite powder was slurried in 80 ml of deionized water at 30° C. While mixing, the Pt solution was added dropwise to the zeolite slurry. The slurry was mixed for 24 hr and then filtered. The solid product was dried for 16 hr at 120° C. It was calcined in a muffle furnace in air by ramping to 400° F. over 2 hr, holding for 10 hr, ramping to 550° F. over 0.5 hr, holding for 3 hr, then cooling in a desiccator before weighing. The catalyst weighed 5.5 g. The powder was then pressed (10,000 psig for 1 min) using a die and hydraulic press to make ½ by ⅜ inch tablets. The tablets were chipped and sized to −20+40 mesh U.S. Standard sieve size. The resulting catalyst contained 0.1 wt % Pt supported on AL-SSZ-33.

Platinum can be added to the other zeolite catalysts in the same manner as described above.

Example 5A—Synthetic T/TMBZ Test Feed

Two similar synthetic test feeds were used in the examples. The feed compositions are shown in the Table below. These feeds were used to compare the performance of various zeolites for T/TMBZ transalkylation. The calculated thermodynamic equilibrium product concentrations at 620° F. for each synthetic feed are also shown.

| Synthetic Feed<br>Component, Wt % | Feed<br>5A-1 | Equil.<br>5A-1 | Feed<br>5A-2 | Equil.<br>5A-2 |
|---|---|---|---|---|
| Benzene | 0.00 | 6.42 | — | 8.46 |
| Toluene | 57.87 | 25.85 | 60.06 | 29.04 |
| Ethylbenzene | 0.03 | — | 0.10 | — |
| Xylenes | 0.00 | 41.60 | — | 40.78 |
| 135 TMBZ | 12.22 | 5.52 | 11.59 | 4.73 |
| 124 TMBZ | 29.54 | 13.80 | 27.88 | 11.84 |
| 123 TMBZ | 0.00 | 1.61 | 0.03 | 1.18 |
| MEBZ* | 0.31 | — | 0.32 | — |
| $C_{10+}$ Aromatics | 0.03 | — | 0.00 | 3.97 |
| Total TMBZ | 41.76 | 20.93 | 39.50 | 17.75 |
| Toluene/TMBZ - Mole/Mole | 1.81 | — | 1.98 | — |
| Ratio Of 124/135 TMBZ | 2.42 | — | 2.42 | — |
| Average Molecular Weight | 102.03 | — | 102.00 | — |

*MEBZ = Methylethylbenzene, also known as ethyltoluene.
**These test feeds do not contain 123 TMBZ. The concentration of this isomer in an equilibrium TMBZ mixture at 550° F. is 7.24 wt %; this small amount was not added. The ratio of the 124 to the 135 TMBZ in the feed is 2.42, which is the ratio of these isomers at equilibrium at 550° F.

Example 5B—A Commercial T/TMBZ Test Feed

A commercial test feed was prepared by blending the heart-cut from commercial C9+ aromatics stream with toluene. The C9+ stream was a reformate heart-cut obtained by distillation. The reformate was produced in a conventional Pt/Re reformer. The weight ratio of toluene to C9+ aromatics was 3 to 2. The composition of this feed is shown below.

| Commercial Test Feed | |
|---|---|
| Component | Wt % |
| C6- | 0.12 |
| Benzene | 0.00 |
| Toluene | 59.47 |
| Ethylbenzene | 0.04 |
| Xylenes | 1.06 |
| Propylbenzenes | 2.51 |
| 135 TMBZ | 4.18 |
| 124 TMBZ | 13.11 |
| 123 TMBZ | 1.89 |
| MEBZ | 15.46 |
| Indan | 0.43 |
| C10+ Aromatics | 1.73 |
| Total TMBZ | 19.18 |
| Toluene/C9 aromatics - Mole/Mole | 2.09 |

Example 6—Performance Testing Procedure

A sample of zeolite (2.2 g) of −20+40 mesh was charged to a 0.5 inch diameter reactor. Inert alundum was placed below and above it. The catalyst was dehydrated by heating in stages to 200° F. in flowing nitrogen and at atmospheric pressure. Then it was heated in stages to 550° F. over a period of 7 hr. After stabilizing at 550° F., the nitrogen was replaced with hydrogen and the pressure increased to 200 psig. With the reactor/catalyst temperature and pressure constant at 550° F. and 200 psig respectively, the hydrogen rate was adjusted so that upon addition of hydrocarbon a H2/HC mole ratio of 3/1 would be achieved. The synthetic feed was then introduced at a rate of 6.0 cc/hr or a WHSV of 2.4 $hr^{-1}$. After a two hour period at 550° F., the reactor effluent was analyzed by an in-line gas chromatograph. The temperature was then increased to 600° F. and after stabilizing at this condition for 2 hr. the reactor effluent was again analyzed by the in-line gas chromatograph. This procedure was repeated as the temperature was increased.

Example 7A—Testing of Al-SSZ-33

Figure 2:
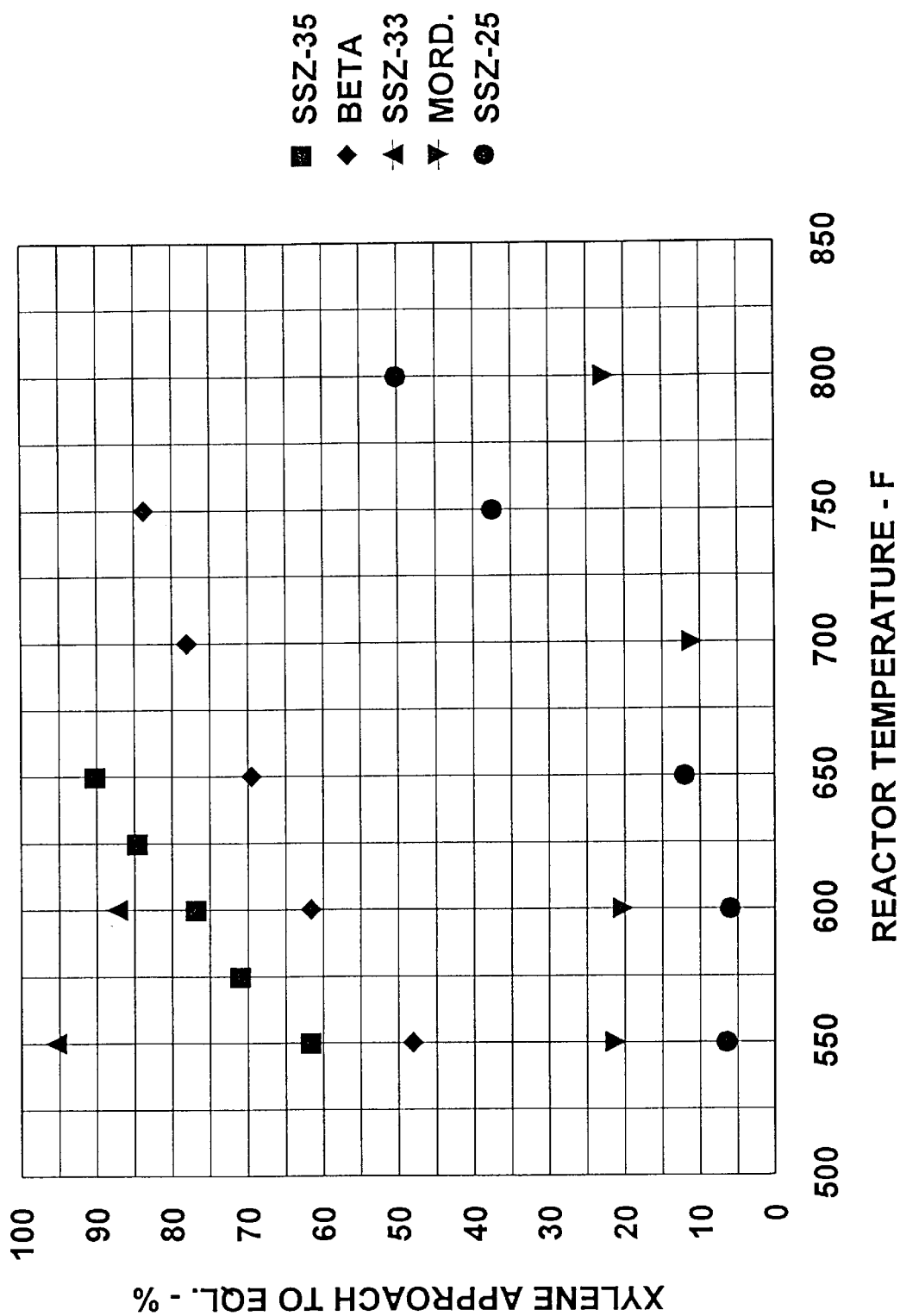
FIG. 2 is a graph comparing the xylene selectivity as a function of temperature for 5 zeolites in the transalkylation of toluene with trimethylbenzene (T/TMBZ). The xylene selectivity is expressed as the xylene approach to equilibrium (XATE).

Ten grams of Al-SSZ-33 zeolite powder prepared as described in Example 1B was formed to particles in the range of −20+40 mesh and charged to the reactor described in Ex. 6. Feed 5A-1 was used, and the procedure of Example 6 was followed. The test results are shown in the Table below. The toluene conversion and Xylene Approach To Equilibrium (XATE) are also shown in FIGS. 1 and 2, respectively, as a function of temperature.

| Al-SSZ-33 | 7A-1 | 7A-2 | Equil. |
|---|---|---|---|
| Hr On Stream | 4.0 | 27.7 | — |
| Temperature, ° F. | 550 | 600 | 620 |
| Component, Wt % | | | |
| C6- | 1.06 | 0.67 | — |
| Benzene | 6.05 | 5.14 | 6.42 |
| Toluene | 30.57 | 28.75 | 25.85 |
| Ethylbenzene | 0.29 | 0.20 | — |
| Xylenes | 39.69 | 36.32 | 41.60 |
| 135 TMBZ | 4.92 | 6.73 | 5.52 |
| 124 TMBZ | 10.53 | 15.03 | 13.80 |
| 123 TMBZ | 1.25 | 1.96 | 1.61 |
| MEBZ | 0.89 | 0.67 | — |
| C10+ Aromatics | 4.50 | 4.52 | — |
| Total | 100.00 | 100.00 | 100.00 |
| Total TMBZ Conversion-Wt % | 16.69 | 23.72 | 20.93 |
| Toluene | 47.18 | 50.32 | 55.33 |
| TMBZ | 60.03 | 43.19 | 49.88 |
| Approach To Equil, % | | | |
| Xylene | 95.4 | 87.3 | 100.0 |
| Benzene | 94.2 | 80.1 | 100.0 |

The equilibrium product distribution shown in the last column is based on Feed 5A-1 reacting at 620° F., based on thermodynamic equilibrium. We assume that one cannot do better than thermodynamic equilibrium, so equilibrium product concentrations are used as a benchmark to determine catalyst performance.

The XATE compares the yield of xylenes (concentration in reactor effluent) obtained at a reaction temperature to that obtained at equilibrium, which for this synthetic feed is 41.6 wt % of feed when the reaction is carried out at 620° F. Thus for Al-SSZ-33, the XATE is 95.4% at 550° F., decreasing to 87.3% at 600° F.

Example 7B—Transalkylation with Ni-Al-SSZ-33

The stability of the zeolites of the invention was vastly improved by impregnating the zeolites with nickel. Thus Ni/Al-SSZ-33 prepared as described in Example 2 was tested with synthetic feed 5A-1 following the procedure of Example 6. However for this particular test, after stabilizing the catalyst at 550° F., this temperature was held for 38.4 hours, after which the temperature was increased to maintain a constant catalyst activity (i.e., a toluene conversion of about 45%). The stability test was discontinued on reaching 555° F. after 123.7 hours on stream. The results are shown in the Table below. Adding nickel reduces catalyst deactivation and enhances long term performance. In addition, the high toluene and TMBZ conversion, about 44 wt % and 54 wt % respectively, are maintained, as is the high xylene yield (XATE of about 90%). Adding nickel stabilized the catalyst but did not decrease the good performance characteristics.

| Ni/Al-SSZ-33 | 7B-1 | 7B-2 | 7B-3 | 7B-4 |
|---|---|---|---|---|
| Hr on Stream | 18.9 | 38.4 | 99.4 | 123.7 |
| Temperature, °F. | 550 | 550 | 553 | 555 |
| Component, wt % | | | | |
| C6– | 3.03 | 2.53 | 1.79 | 1.66 |
| Benzene | 4.81 | 6.39 | 5.22 | 5.19 |
| Toluene | 28.12 | 32.5 | 31.98 | 32.12 |
| Ethylbenzene | 0.28 | 0.26 | 0.18 | 0.17 |
| Xylenes | 39.62 | 37.45 | 37.91 | 37.27 |
| 135 TMBZ | 5.46 | 4.59 | 5.61 | 5.67 |
| 124 TMBZ | 11.82 | 9.76 | 11.94 | 12.07 |
| 123 TMBZ | 1.47 | 1.21 | 1.47 | 1.50 |
| MEBZ | 1.07 | .85 | 0.66 | 0.63 |
| C10+ Aromatics | 4.3 | 4.47 | 3.24 | 3.75 |
| Total | 100.00 | 100.00 | 100.00 | 100.00 |
| Total TMBZ | 18.75 | 15.55 | 19.03 | 18.24 |
| Conversion-wt % | | | | |
| Toluene | 51.40 | 43.84 | 44.74 | 44.50 |
| TMBZ | 55.11 | 62.76 | 54.44 | 53.94 |
| Approach to Equil, % | | | | |
| Xylene | 95.2 | 90.0 | 91.1 | 89.6 |
| Benzene | 74.9 | 99.5 | 81.3 | 80.8 |

Example 7C—Testing of Pd-Al-SSZ-33

Al-SSZ-33 was impregnated to add 0.1 wt % palladium as described in Example 3. The catalyst was tested using synthetic feed 5A-1 as described in Example 6. The results are shown in the Table below.

| Al-SSZ-33 | 7C-1 (Pd) | 7C-2 (Pd) | 7C-3 (Pd) | 7D (Pt) |
|---|---|---|---|---|
| Hr on Stream | 3.9 | 27.2 | 31.7 | 5.2 |
| Temperature, °F. | 550 | 600 | 650 | 550 |
| Component, wt % | | | | |
| C6– | 3.92 | 4.04 | 4.66 | 77.83 |
| Benzene | 5.74 | 5.49 | 5.79 | 0.15 |
| Toluene | 30.56 | 27.82 | 27.01 | 1.75 |
| Ethylbenzene | 0.34 | .39 | 0.44 | 0.04 |
| Xylenes | 39.94 | 38.28 | 36.51 | 7.54 |
| 135 TMBZ | 4.77 | 4.81 | 4.53 | 2.86 |
| 124 TMBZ | 10.14 | 10.65 | 10.42 | 6.00 |
| 123 TMBZ | 1.23 | 1.39 | 1.44 | 0.68 |
| MEBZ | 1.08 | 1.24 | 1.31 | 0.39 |
| C10+ Aromatics | 2.28 | 6.10 | 7.88 | 2.76 |
| Total | 100.00 | 100.00 | 100.00 | 100.00 |
| Total TMBZ | 16.15 | 16.85 | 16.39 | 9.54 |
| Conversion-wt % | | | | |
| Toluene | 47.20 | 52.27 | 53.32 | 96.98 |
| TMBZ | 61.34 | 59.66 | 60.74 | 77.16 |
| Approach to Equil, % | | | | |
| Xylene | 96.0 | 92.0 | 87.8 | 18.1 |
| Benzene | 89.3 | 85.5 | 90.2 | 2.3 |

Comparative Example 7D—Pt-Al-SSZ-33

Al-SSZ-33 containing 0.1 wt % Pt was prepared as described in Example 4 and tested using the procedure of Example 6 with synthetic feed 5A-1. The Table above shows the results after 5.2 hr on stream. The toluene conversion is extremely high at 96.98 wt %, and the TMBZ conversion of 77.16 wt % is also high. These conversions are well in excess of the maximum equilibrium conversions of 55.33 wt % and 49.88 wt % for toluene and TMBZ respectively, if TMBZ was transalkylating toluene. Also the C6-yield is extremely high at 77.83 wt %. Together the data indicates a substantial hydrogenation of the aromatic rings has taken place, followed by cracking of the resulting naphthenes and hydrogenation of the cracked products. Similar results were also obtained at 22.1 hr on stream at 550° F., even though some slight deactivation of the catalyst had occurred, and after the temperature had been reduced to 450° F. In spite of the low Pt concentration (0.1 wt %), substantial undesirable hydrogenation of the aromatic ring occurred.

Example 8A—Test of SSZ-35

SSZ-35 prepared as in Example 1C was tested in the same manner as described in Example 6 using synthetic feed 5A-1. The results with SSZ-35 are shown in the Table below. The toluene conversion and XATE are shown as a function of temperature in FIGS. 1 and 2 respectively.

| SSZ-35 | 8 A-1 | 8 A-2 | 8 A-3 | 8 A-4 | 8 A-5 |
|---|---|---|---|---|---|
| Hr on Stream | 4.9 | 9.8 | 28.4 | 32.7 | 50.4 |
| Temperature, °F. | 550 | 575 | 600 | 625 | 650 |
| Component, wt % | | | | | |
| C6– | 0.24 | 0.24 | 0.24 | 0.33 | .37 |
| Benzene | 9.69 | 8.39 | 7.44 | 7.70 | 6.95 |
| Toluene | 37.04 | 32.04 | 29.27 | 29.56 | 28.67 |
| Ethylbenzene | 0.05 | .07 | 0.07 | 0.09 | 0.10 |
| Xylenes | 25.61 | 29.51 | 31.96 | 35.18 | 37.47 |
| 135 TMBZ | 9.4 | 10.21 | 10.61 | 8.85 | 8.06 |
| 124 TMBZ | 15.23 | 16.00 | 16.34 | 14.12 | 13.78 |
| 123 TMBZ | 1.81 | 2.05 | 2.19 | 1.91 | 1.9 |
| MEBZ | 0.12 | 0.15 | 0.16 | .23 | 0.27 |
| C10+ Aromatics | 0.78 | 1.34 | 1.72 | 2.04 | 2.42 |
| Total | 100.00 | 100.00 | 100.00 | 100.00 | 100.00 |
| Total TMBZ | 26.45 | 28.27 | 29.13 | 24.87 | 23.73 |
| Conversion-wt % | | | | | |
| Toluene | 35.98 | 44.63 | 49.41 | 48.92 | 50.46 |
| TMBZ | 36.67 | 32.31 | 30.24 | 40.45 | 43.17 |
| Approach to Equil, % | | | | | |
| Xylene | 61.6 | 70.9 | 76.8 | 84.6 | 90.1 |
| Benzene | 150.9 | 130.7 | 115.9 | 119.9 | 108.3 |

The toluene conversion reached 50.5 wt % at 650° F. compared to the maximum toluene conversion of 55.33%, which can be achieved with this feed based on equilibrium considerations. In addition the xylene yield of 37.47 wt % of feed represents 90.1% of the xylene yield at equilibrium is (41.6 wt %).

Example 8B—Ni/SSZ-35

Figure 3:
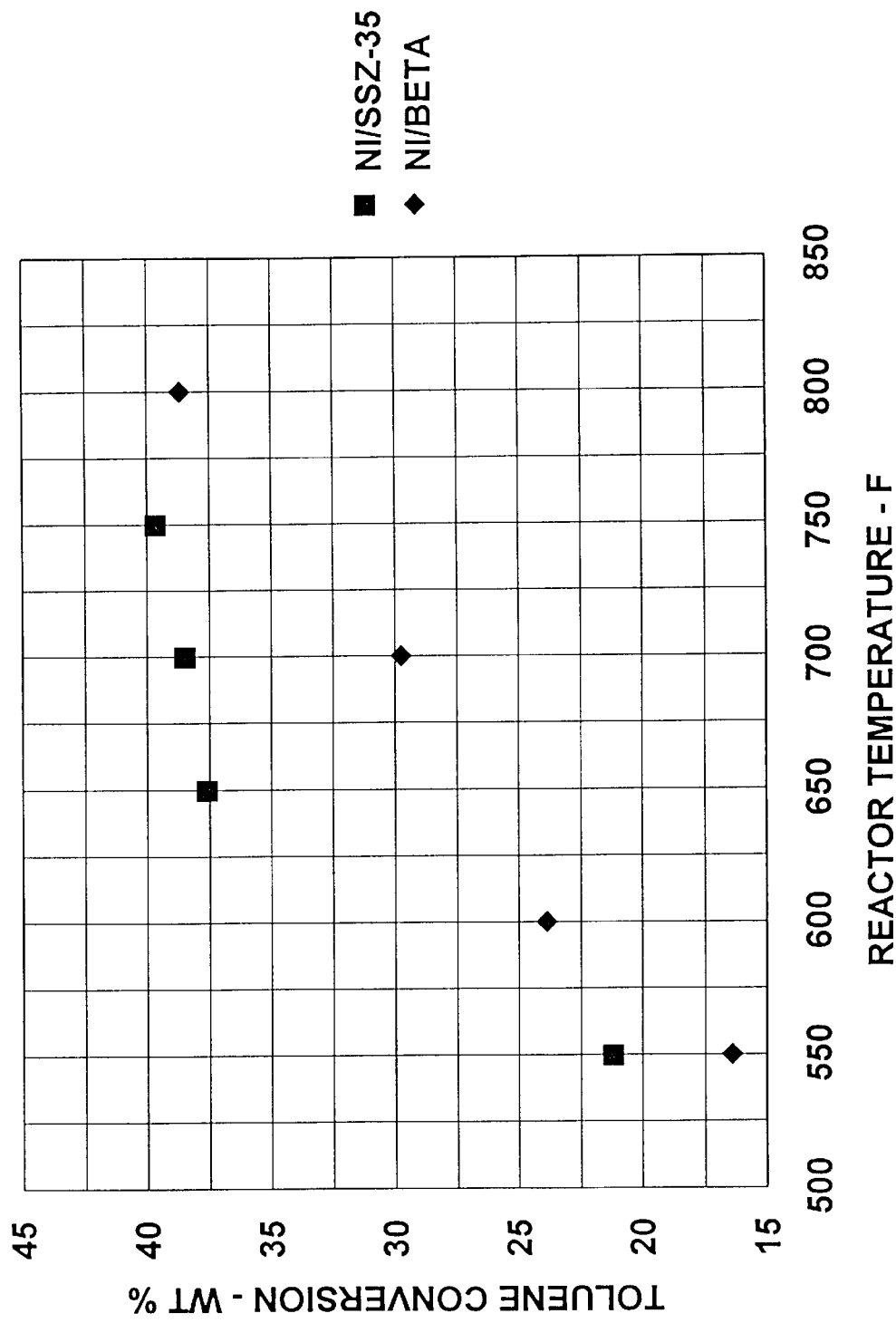
FIG. 3 is a graph comparing the catalytic performance of 3 zeolites in the transalkylation of toluene with a commercial C9+ aromatics feed. The wt % toluene conversion is shown as a function of temperature.

SSZ-35 impregnated with nickel, prepared as described in Example 2, was tested as described in Example 6 using synthetic feed 5A-2, except that the temperature was increased from an initial temperature of 550° F. to 675° F., at which point the XATE was in excess of 90%. After stabilizing the catalyst at 675 ° F., the catalyst temperature was increased to maintain this catalyst activity and performance, i.e. a toluene conversion of about 50%. The results are shown in the Table below. Toluene conversion as a function of temperature is shown in FIG. 3. The addition of nickel stabilized the catalyst without impairing its performance. The catalyst activity observed (in Example 8A) at 650° F. is essentially maintained by increasing the temperature by 25° F. to 675° F. At that temperature the toluene conversion is about 50% as in (Example 8A) at 650° F. This is indeed a very high toluene conversion when compared to the maximum possible toluene conversion of 51.65 wt %, i.e. 96.8% of maximum. However note that the TMBZ conversion is higher, namely, about 50–54% versus about 43% in (Example 8A). The maximum desirable TMBZ conversion is 47.0 wt % based on equilibrium considerations. In addition, the xylene yield and the selectivity to xylene are higher as evidenced by a XATE of 95.9–97.5% versus 90.1% (in Example 8A).

| Ni/SSZ-35 | 8B-1 | 8B-2 | 8B-3 | 8B-4 | 8B-5 |
|---|---|---|---|---|---|
| Hr on Stream | 71.0 | 74.3 | 79.4 | 144.4 | 149.4 |
| Temperature, °F. | 650 | 675 | 675 | 681 | 682 |
| Component, wt % | | | | | |
| C6– | 0.92 | 1.27 | 1.26 | 1.19 | 1.05 |
| Benzene | 7.85 | 6.88 | 7.10 | 7.43 | 6.86 |
| Toluene | 31.12 | 28.86 | 29.05 | 31.07 | 29.36 |
| Ethylbenzene | 0.14 | 0.16 | 0.15 | 0.18 | 0.18 |
| Xylenes | 37.07 | 39.04 | 37.76 | 39.10 | 39.76 |
| 135 TMBZ | 5.83 | 5.72 | 5.58 | 4.89 | 5.35 |
| 124 TMBZ | 12.83 | 13.13 | 13.10 | 11.35 | 12.38 |
| 123 TMBZ | 1.71 | 1.82 | 1.89 | 1.55 | 1.71 |
| MEBZ | 0.27 | 0.41 | 0.4 | 0.40 | 0.47 |
| C10+ Aromatics | 2.26 | 2.71 | 3.72 | 2.84 | 2.88 |
| Total | 100.00 | 100.00 | 100.00 | 100.00 | 100.00 |
| Total TMBZ Conversion-wt % | 20.37 | 20.67 | 20.57 | 17.79 | 19.44 |
| Toluene | 48.19 | 51.95 | 51.64 | 48.27 | 51.11 |
| TMBZ | 48.43 | 47.67 | 47.93 | 54.97 | 50.79 |
| Component, wt % | | | | | |
| Xylene | 90.1 | 95.7 | 92.6 | 95.9 | 97.5 |
| Benzene | 92.8 | 81.3 | 83.9 | 87.9 | 81.1 |

Example 8C—Testing of Ni/SSZ-35 with Commercial Feed

SSZ-35 impregnated with 1 wt % nickel was prepared as described in Example 2. It was tested as described in Example 6 using the Commercial Feed 5B, except that the temperature was increased from an initial temperature of 550° F. to 750° F. in 50° F. increments, after which the temperature was reduced to 700° F. After stabilizing the catalyst at 700° F., the catalyst temperature was increased to maintain the catalyst activity and performance achieved at 700° F., i.e., a toluene conversion of about 39 wt %. The results are shown in the Table below. Toluene conversion as a function of temperature is also shown in FIG. 3. Best results are achieved at 700° F. where the toluene conversion is about 39% and the TMBZ conversion is about 50%. In addition, the propylbenzene (PBZ) conversion is 100% and surprisingly the methylethylbenzene (MEBZ) conversion is about 95%. This is an extremely high MEBZ conversion and is very advantageous, since the products are toluene and ethane. The toluene made from the MEBZ, as well as the converted toluene that does not react with TMBZ, can be disproportionated to xylene and benzene, adding to the overall make xylenes and benzene. The selectivity to xylenes is about 87–91%, and 104–112% for benzene. Another important advantage of having 90+% MEBZ conversion is that less of this material is recycled to the reactor in a commercial process, resulting in savings in capital investment and operating costs.

| Ni - SSZ-35 | 8C-1 | 8C-2 | 8C-3 | 8C-4 | 8C-5 | 8C-6 |
|---|---|---|---|---|---|---|
| Hr on Stream | 4.0 | 9.2 | 26.8 | 30.9 | 33.8 | 153.9 |
| Temperature, °F. | 550 | 650 | 700 | 750 | 700 | 712 |
| Component, wt % | | | | | | |
| C6– | 2.26 | 5.13 | 6.46 | 9.95 | 6.24 | 6.09 |
| Benzene | 6.63 | 12.82 | 13.43 | 13.92 | 13.29 | 13.30 |
| Toluene | 46.88 | 37.13 | 36.59 | 35.90 | 36.28 | 36.31 |
| Ethylbenzene | 1.07 | 1.23 | 0.54 | 0.33 | 0.59 | 0.73 |
| Xylenes | 13.50 | 29.24 | 30.79 | 28.73 | 30.22 | 30.32 |
| PBZ | 0.91 | 0.00 | 0.00 | 0.00 | 100.00 | 0.00 |
| 135 TMBZ | 4.18 | 3.03 | 2.55 | 2.17 | 2.45 | 2.49 |
| 124 TMBZ | 9.78 | 6.60 | 6.03 | 5.32 | 5.78 | 5.83 |
| 123 TMBZ | 1.24 | 0.87 | 0.86 | 0.76 | 0.83 | 0.83 |
| MEBZ | 10.79 | 1.87 | 0.77 | 0.46 | 0.77 | 1.04 |
| Indan | 0.12 | 0.09 | 0.05 | 0.03 | 0.04 | 0.06 |
| C10+ Aromatics | 2.63 | 1.98 | 1.93 | 2.42 | 3.50 | 3.00 |
| Total | 100.00 | 100.00 | 100.00 | 100.00 | 100.00 | 100.00 |
| Total TMBZ Conversion-wt % | 15.2 | 10.50 | 9.44 | 8.26 | 9.06 | 9.15 |
| Toluene | 21.17 | 37.57 | 38.47 | 39.64 | 39.00 | 38.95 |
| TMBZ | 20.75 | 45.27 | 50.76 | 56.96 | 52.75 | 52.28 |
| PBZ | 63.75 | 100.00 | 100.00 | 100.00 | 100.00 | 100.00 |
| MEBZ | 30.22 | 87.89 | 95.02 | 97.04 | 95.01 | 93.30 |
| Selectivity-% | | | | | | |
| Xylenes | 85.30 | 92.75 | 91.28 | 79.8 | 87.70 | 88.67 |
| Benzene | 109.10 | 102.14 | 104.75 | 110.97 | 111.54 | 109.56 |
| C8 Aromatics Distribution-% | | | | | | |
| EB | 7.37 | 4.05 | 1.71 | 1.13 | 1.92 | 2.36 |
| Xylenes | 92.63 | 95.95 | 98.29 | 98.87 | 98.08 | 97.64 |

Comparative Example 9—Beta Zeolite

Beta zeolite extrudate was obtained from PQ Corporation, Pennsylvania. The extrudate consisted of 65 wt % zeolite and 35 wt % alumina binder. This zeolite, like all the zeolites tested, had been exchanged and calcined to the hydrogen form and was tested as described in Example 6 with synthetic feed 5A-1, except that 2.7 grams of crushed extrudate was charged to the reactor. The resulting WHSV based on the zeolite content was 3.0 hr$^{-1}$. The results are shown in the Table below. The toluene conversion and the XATE are shown as a function of temperature in FIGS. 1 and 2 respectively.

| Beta zeolite | 9-1 | 9-2 | 9-3 | 9-4 | 9-5 |
|---|---|---|---|---|---|
| Hr on Stream | 8.4 | 32.9 | 53.2 | 59.2 | 62.9 |
| Temperature, ° F. | 550 | 600 | 650 | 700 | 750 |
| Component, wt % | | | | | |
| C6− | 0.31 | 0.32 | 0.34 | 0.55 | 0.85 |
| Benzene | 1.61 | 2.19 | 2.91 | 4.41 | 6.15 |
| Toluene | 61.62 | 53.19 | 46.95 | 43.90 | 41.56 |
| Ethylbenzene | 0.04 | 0.05 | 0.06 | 0.09 | 0.13 |
| Xylenes | 19.99 | 25.64 | 28.90 | 32.45 | 34.81 |
| 135 TMBZ | 4.47 | 4.71 | 4.90 | 4.04 | 3.50 |
| 124 TMBZ | 9.47 | 10.26 | 11.37 | 9.74 | 8.50 |
| 123 TMBZ | 0.99 | 1.26 | 1.53 | 1.36 | 1.20 |
| MEBZ | 0.18 | 0.25 | 0.23 | 0.29 | 0.34 |
| C10+ Aromatics | 1.32 | 2.14 | 2.77 | 3.15 | 2.97 |
| Total | 100.00 | 100.00 | 100.00 | 100.00 | 100.00 |
| Total TMBZ | 14.93 | 16.22 | 17.80 | 15.15 | 13.20 |
| Conversion-wt % | | | | | |
| Toluene | (6.48) | 8.09 | 18.87 | 24.13 | 28.19 |
| TMBZ | 64.25 | 61.16 | 57.38 | 63.72 | 68.39 |
| Approach to Equil, % | | | | | |
| Xylene | 48.1 | 61.6 | 69.5 | 78.0 | 83.7 |
| Benzene | 25.1 | 34.1 | 45.3 | 68.7 | 95.8 |

Beta zeolite is much less active than either Al-SSZ-33 or SSZ-35, that is, at the same temperature the toluene conversion is much lower. Thus at 650° F., the toluene conversion with SSZ-35 is 50.46 wt % compared to 18.87 wt % with beta zeolite. Even at 750° F. the toluene conversion is only 28.2 wt %. Also, the xylenes make is lower with beta zeolite. At 650° F., the XATE is 90.1% with SSZ-35 versus 69.5% with beta zeolite. The lower operating temperature of SSZ-35 is advantageous, as it should result in a lower catalyst deactivation rate due to coking. Although with beta zeolite the XATE increased to 83.7% as the temperature was increased to 750° F., the toluene conversion at 28.2 wt % is still low, however the TMBZ conversion increased to 68.4 wt %. This indicates that the increase in xylenes make and hence XATE is due to degradation of the TMBZ—a distinct disadvantage. From this, it is clear that SSZ-35 is a better catalyst than beta zeolite—it can operate at a lower temperature, convert a higher quantity of toluene via reaction with TMBZ to the primary product (xylenes) and does not degrade TMBZ to lighter aromatics as does beta zeolite.

Comparative Example 10A—Testing of Ni/Beta Zeolite

Beta zeolite powder with a silica to alumina ratio of about 25–30 was obtained from PQ Corporation, Pennsylvania. A catalyst containing 1 wt % nickel was prepared in the manner described in Ex. 2. It was tested as described in Example 6 using synthetic feed 5A-2. The initial temperature was 550° F. This was gradually increased to 650° F., at which point the XATE was in excess of 90%. The catalyst was stabilized at 650° F. and then the temperature was increased to maintain this catalyst activity and performance, i.e. a toluene conversion of about 39 wt %. The toluene conversion reached 39.8 wt % at 57.8 hr with a TMBZ conversion of about 58 wt % at 650° F. Catalyst temperature was increased at the rate of 0.12° F./hr however toluene conversion decreased to about 36 wt % at 99.6 hr. This compares to a temperature increase at the rate of 0.09° F./hr to maintain 48–51 wt % toluene conversion for Ni/SSZ-35 as shown in Ex 8B. This indicates that Ni/SSZ-35, a catalyst of the invention, is more stable than Ni/Beta zeolite at the same Ni loading. In addition, yield of the desired products—BZ and xylenes—with Ni/SSZ-35 is higher than with Ni/Beta zeolite at the same temperature. Thus at 650° F. and 71.0 hr in Ex 8B-1, the yield with Ni/SSZ-35 is 0.93 gm/gm of feed reacted, compared to 0.89 gm/gm of feed reacted with Ni/Beta zeolite at 650° F. and 57.8 hr. Thus as shown in Ex 9, beta zeolite is less selective than SSZ-35.

| Ni/Beta Zeolite | 10A-1 | 10A-2 | 10A-3 | 10A-4 |
|---|---|---|---|---|
| Hr on Stream | 51.2 | 57.8 | 71.7 | 99.6 |
| Temperature, ° F. | 650 | 650 | 652 | 655 |
| Component, wt % | | | | |
| C6− | 1.04 | 1.05 | 0.87 | 0.67 |
| Benzene | 3.51 | 3.73 | 3.50 | 3.17 |
| Toluene | 31.70 | 36.18 | 37.94 | 38.24 |
| Ethylbenzene | 0.24 | 0.19 | 0.16 | 0.13 |
| Xylenes | 39.11 | 38.02 | 37.73 | 36.91 |
| 135 TMBZ | 5.04 | 4.44 | 4.43 | 4.70 |
| 124 TMBZ | 12.03 | 10.81 | 10.39 | 11.04 |
| 123 TMBZ | 1.68 | 1.41 | 1.47 | 1.55 |
| MEBZ | 1.2 | 0.85 | 0.69 | 0.63 |
| C10+ Aromatics | 4.45 | 3.32 | 2.83 | 2.97 |
| Total | 100.00 | 100.00 | 100.00 | 100.00 |
| Total TMBZ | 18.75 | 16.66 | 16.29 | 17.28 |
| Conversion-wt % | | | | |
| Toluene | 47.21 | 39.76 | 36.83 | 36.33 |
| TMBZ | 52.53 | 57.82 | 58.76 | 56.25 |
| Approach to Equil, % | | | | |
| Xylene | 95.91 | 93.23 | 92.53 | 90.51 |
| Benzene | 41.51 | 44.07 | 41.34 | 37.45 |

Comparative Example 10B—Ni/Beta Zeolite with Commercial Feed

Beta zeolite containing 1 wt % nickel was prepared in the manner described in Example 2. It was tested as described in Example 6 using commercial feed (5B) over a temperature range that varied from 550 to 800° F. The results are shown in the Table below. Toluene conversion as a function of temperature is also shown in FIG. 3. Maximum toluene conversion of 39.7 wt % was reached at 800° F. This is 50 to 100° F. higher than the temperature required with Ni/SSZ-35 to achieve a similar toluene conversion. The same is true of the xylenes yield, namely, the maximum xylenes yield of 29.1 wt % with Ni/Beta zeolite is achieved at 800° F., compared to a xylenes yield of 30.8 wt % at 700° F. with Ni/SSZ-35. Thus as observed earlier, Ni/Beta zeolite is about 100° F. less active than Ni/SSZ-35, a catalyst of the invention. Note that operation with Ni/Beta zeolite at a temperature 100° F. higher than with Ni/SSZ-35 results in a substantially higher catalyst deactivation rate for Ni/Beta zeolite. Also as seen in previous examples with beta zeolite, it has a much higher TMBZ conversion than SSZ-35. This high TMBZ conversion is due to degradation of TMBZ to lighter aromatics, which is not a desirable use of TMBZ. Rather, it is desired that xylenes be formed by reaction with toluene, as this results in a higher yield of products (i.e., xylene and benzene) per unit of reactants (toluene and TMBZ). In other words, reaction of one mole of toluene with one mole of TMBZ gives two moles of xylenes. Whereas, dealkylation of one mole of TMBZ results in formation of one mole of xylenes or if the process continues, one mole of toluene or one mole of benzene. Thus a low toluene conversion coupled with a high TMBZ conversion suggests undesirable dealkylaton of TMBZ.

Also, Ni/Beta zeolite overall has a lower MEBZ conversion than Ni/SSZ-35. The maximum value of 83.8 wt % reached at 800° F. is well below the 95% conversion obtained with Ni/SSZ-35 at 700° F. The xylenes selectivity reached a maximum value of 89.3% at 700° F. This is close to the value of 91.3% obtained with Ni/SSZ-35 at 700° F. The problem with the Ni/Beta zeolite is that at 700° F., the toluene conversion is only 28–30 wt % compared to about 39.0 wt % with Ni/SSZ-35 also at 700° F. Finally, the C8 aromatics distribution shows that Ni/Beta zeolite makes more ethylbenzene (EB) than Ni/SSZ-35. EB is undesirable from a para-xylene production standpoint. At 700° F., the EB content on a C8 aromatics basis is 8.8 wt % for Ni/Beta zeolite versus 1.7–1.9 wt % for Ni/SSZ-35, or a factor of five higher for Ni/Beta zeolite. From the above, it should be apparent that the catalyst of the invention is more advantageous than Ni/Beta zeolite. The catalyst of the invention is more active from a toluene conversion standpoint, has a higher xylenes selectivity, has a higher MEBZ conversion and makes a lot less undesirable ethylbenzene.

| Ni/Beta Zeolite | 10B-1 | 10B-2 | 10B-3 | 10B-3 |
|---|---|---|---|---|
| Hr on Stream | 4.7 | 8.9 | 30.8 | 33.4 |
| Temperature, ° F. | 550 | 600 | 700 | 800 |
| Component, wt % | | | | |
| C6− | 2.73 | 2.34 | 3.43 | 7.79 |
| Benzene | 4.26 | 4.88 | 6.86 | 11.44 |
| Toluene | 49.71 | 45.27 | 41.78 | 36.47 |
| Ethylbenzene | 2.94 | 2.93 | 2.69 | 1.52 |
| Xylenes | 24.57 | 25.92 | 27.93 | 29.05 |
| PBZ | 0.35 | 0.28 | 0.08 | 0.05 |
| 135 TMBZ | 1.69 | 1.95 | 2.01 | 2.03 |
| 124 TMBZ | 3.59 | 4.39 | 4.84 | 5.07 |
| 123 TMBZ | 0.44 | 0.58 | 0.58 | 0.28 |
| MEBZ | 6.94 | 7.13 | 5.62 | 2.51 |
| Indan | 0.24 | 0.32 | 0.29 | 0.15 |
| C10+ Aromatics | 2.54 | 4.01 | 3.89 | 3.65 |
| Total | 100.00 | 100.00 | 100.00 | 100.00 |
| Total TMBZ Conversion-wt % | 5.72 | 6.93 | 7.43 | 7.37 |
| Toluene | 16.41 | 23.88 | 29.75 | 38.68 |
| TMBZ | 70.17 | 63.89 | 61.25 | 61.59 |
| PBZ | 85.88 | 88.85 | 96.80 | 98.21 |
| MEBZ | 55.10 | 53.89 | 63.66 | 83.78 |
| Selectivity-% | | | | |
| Xylenes | 86.37 | 88.49 | 89.27 | 80.86 |
| Benzene | 122.99 | 100.20 | 95.21 | 107.84 |
| C8 Aromatics Distribution-% | | | | |
| EB | 10.70 | 10.16 | 8.79 | 4.98 |
| Xylenes | 89.30 | 89.84 | 91.21 | 95.02 |

Comparative Example 11—Mordenite

The acid form of a mordenite with a silica to alumina mole ratio of about 15 was obtained from Tosoh Corp. and tested as described in Example 6 with synthetic feed 5A-1. The results with this mordenite are shown in the Table below and in FIGS. 1 and 2. The mordenite was very unstable and, as a result, the levels of toluene conversion were low even though the temperature was rapidly increased to 800° F. over 30 hours. The low toluene conversion results in a low xylene make and hence a low XATE. Clearly, the zeolites of the invention are more advantageous than mordenite. The toluene and TMBZ conversions are higher and near equilibrium, and the xylene yield as measured by the XATE is also higher.

| Mordenite | 11-1 | 11-2 | 11-3 | 11-4 |
|---|---|---|---|---|
| Hr on Stream | 3.7 | 7.0 | 28.4 | 29.9 |
| Temperature, ° F. | 550 | 600 | 700 | 800 |
| Component, wt % | | | | |
| C6− | 0.12 | 0.16 | 0.25 | .86 |
| Benzene | 1.14 | 1.15 | 0.66 | 1.31 |
| Toluene | 54.61 | 50.75 | 55.62 | 52.33 |
| Ethylbenzene | 0.03 | 0.03 | 0.00 | 0.29 |
| Xylenes | 8.82 | 8.39 | 4.6 | 9.4 |
| 135 TMBZ | 10.45 | 11.49 | 10.56 | 9.26 |
| 124 TMBZ | 20.00 | 24.06 | 24.32 | 22.51 |
| 123 TMBZ | 2.43 | 3.15 | 3.42 | 3.37 |
| MEBZ | 0.24 | 0.29 | 0.23 | 0.29 |
| C10+ Aromatics | 2.17 | 0.53 | 0.34 | 0.65 |
| Total | 100.00 | 100.00 | 100.00 | 100.00 |
| Total TMBZ Conversion-wt % | 32.87 | 38.71 | 38.31 | 35.13 |
| Toluene | 5.62 | 12.29 | 3.89 | 9.56 |
| TMBZ | 21.28 | 7.32 | 8.27 | 15.87 |
| Approach To Equil., % | | | | |
| Xylene | 21.2 | 20.2 | 11.0 | 22.6 |
| Benzene | 17.8 | 17.9 | 10.3 | 20.4 |

The zeolites of the invention in the absence of added metals, as well as those not of the invention, all showed some deactivation, the worst being the mordenite described in Example 11.

Example 12—Transalkylation Using Ni/SSZ-44

SSZ44 was prepared as in Ex. 1E. Nickel was added as described in Ex. 2. This zeolite was tested using commercial feed 5B under the operating conditions described in Example 6. Zeolite SSZ-44 was shown to be an effective catalyst for the gas phase transalkylation of toluene with TMBZ.

Comparative Example 13

Liquid Phase T/TMBZ Transalkylation with SSZ-35 Using Commercial Feed

This comparative example shows the performance of SSZ-35, a catalyst useful in the present gas phase process, in liquid phase transalkylation. A gas phase process using SSZ-35 is shown in Ex. 8A, and a gas phase process using Ni-SSZ-35 is shown in Ex. 8B and 8C.

Toluene was transalkylated by TMBZ contained in commercial feed 5B under liquid phase conditions using SSZ-35. 5.25 g catalyst, with a particle size range of from −20+40 mesh, was charged to a 0.5-inch diameter reactor. The catalyst was dehydrated at 200° F. in flowing N2 at 15 psig. Then the temperature was increased to 500° F. Thereafter, the pressure was increased to 400 psig with nitrogen and feed was introduced at the rate of 6 cc/hr. Nitrogen flow was stopped after ½ hr. The reactor effluent was cooled by refrigeration, and liquid samples were collected over time and analyzed by gas chromatography. Samples were collected after 6 hr on stream, when all the nitrogen originally in the reactor had eluted out. Off-gas generated was less than 1 wt % of the feed to the catalyst. Operating conditions were a pressure of 400 psig, a WHSV of 1.0-hr−1 and a temperature of 500° F. No hydrogen was used. During the course of the experiment, the catalyst temperature was held at 500° F. to maintain liquid phase conditions. At 400 psig, toluene vaporization occurs at 550° F. The results are shown in the table below.

| Liquid Phase | 13-A | 13-B | 13-C | 13-D | 13-E | 13-F |
|---|---|---|---|---|---|---|
| Hr On Stream | 6–8 | 23–25 | 47–50 | 56–71 | 75–79 | 95–99 |
| Temperature, ° F. | 500 | 500 | 500 | 500 | 500 | 500 |
| Component | | | | | | |
| C6− | 0.09 | 0.16 | 0.15 | 0.30 | 0.15 | 0.21 |
| Benzene | 8.02 | 9.38 | 8.10 | 8.76 | 7.57 | 7.25 |
| Toluene | 28.52 | 31.29 | 35.01 | 38.13 | 39.21 | 41.09 |
| Ethylbenzene | 3.63 | 2.07 | 1.26 | 1.02 | 0.89 | 0.74 |
| Xylenes | 25.86 | 20.80 | 17.10 | 15.22 | 14.30 | 12.83 |
| PBZ | 0.67 | 1.22 | 1.51 | 1.54 | 1.63 | 1.66 |
| 135 TMBZ | 4.75 | 4.59 | 4.62 | 4.43 | 4.55 | 4.46 |
| 124 TMBZ | 9.17 | 10.61 | 11.64 | 11.39 | 11.91 | 11.87 |
| 123 TMBZ | 1.43 | 1.55 | 1.65 | 1.60 | 1.67 | 1.66 |
| MEBZ | 9.04 | 11.61 | 13.23 | 13.15 | 13.77 | 13.82 |
| Indan | 0.39 | 0.26 | 0.19 | 0.16 | 0.15 | 0.13 |
| C10+ Aromatics | 8.43 | 6.45 | 5.54 | 4.31 | 4.20 | 4.28 |
| Total | 100.00 | 100.00 | 100.00 | 100.00 | 100.00 | 100.00 |
| Total TMBZ Conversion-wt % | 16.35 | 16.75 | 17.92 | 17.42 | 18.13 | 18.00 |
| Toluene | 52.04 | 47.38 | 41.12 | 35.89 | 34.07 | 30.91 |
| TMBZ | 19.98 | 12.66 | 6.59 | 9.18 | 5.47 | 6.15 |
| PBZ | 73.41 | 51.55 | 39.84 | 38.65 | 35.06 | 33.86 |
| MEBZ Selectivity-% | 41.52 | 24.90 | 14.44 | 14.96 | 10.94 | 10.64 |
| Xylenes | 96.35 | 93.34 | 95.80 | 90.46 | 95.87 | 91.41 |
| Benzene | 71.25 | 89.34 | 88.84 | 104.87 | 95.46 | 103.43 |
| C8 Aromatics Distribution, % | | | | | | |
| EB | 12.32 | 9.06 | 6.84 | 6.26 | 5.84 | 5.46 |
| Xylenes | 87.68 | 90.94 | 93.16 | 93.74 | 94.16 | 94.54 |

The results show that catalyst activity declined with time, as evidenced by the decrease in conversion of toluene, TMBZ, MEBZ and PBZ. More importantly, while the initial toluene conversion was 55.91 wt %, the TMBZ conversion was extremely low, namely, 19.98 wt %. The low TMBZ conversion, substantially higher toluene conversion and low xylene yield all suggest that toluene disproportionation (TDP) is the primary mechanism by which xylenes are formed. Here, TDP is a less desirable reaction than T/TMBZ, as it results in a lower yield of xylenes (wt. xylenes/wt. reactants).

The relatively poor performance of SSZ-35 in the (partial) liquid phase T/TMBZ reaction is in contrast to the excellent performance of this catalyst in the gas phase process (See Example 8A), where TMBZ conversion is about 50 wt %. Here the primary route for making xylenes is transalkylation of toluene by TMBZ . As noted above, transalkylation produces more xylenes than TDP, when xylene yield is expressed as wt. xylenes/wt. reactants. Also note that in the liquid phase process, the xylene yield is 25.9 wt % declining with time to 12.8 wt %. This initial xylene yield is about 16 wt % lower than the 30.8 wt % achieved in a gas phase process with Ni/SSZ-35 at 700 ° F. as shown in Example 8B. An advantage of the gas phase process is that the catalyst is very stable and the xylene yield is maintained over a long period of time with a slight adjustment in temperature. However, the catalyst of the liquid phase process is much less stable and, because of the need to stay in the liquid phase, catalyst activity declines cannot be compensated for over the long term with temperature increases. Thus, at end-of run, the xylene yield with the liquid phase process is 57 wt % lower than the comparable yield with the gas phase process. It is clear that the gas phase process is significantly better than the liquid phase T/TMBZ transalkylation process when using SSZ-35.

Example 14—Toluene Disproportionation Using Ni/Al-SSZ-33

Ni/Al-SSZ-33 was prepared in the manner of Example 2 and was tested for gas phase toluene disproportionation.. Operating conditions were as described in Example 6, except that the WHSV was 5.8 hr−1. The catalyst was tested at 550° F., 600° F. and 650° F. Feed purity was 99.98 wt % toluene. The results are shown in below and are compared to the equilibrium yields at 620° F.

| Toluene Disproportionation | 14A | 14B | 14C | Eq. Distr.[1] |
|---|---|---|---|---|
| Hr on Stream | 8.1 | 27.1 | 31.0 | |
| Temperature, F. | 550 | 600 | 650 | 620 |
| Component | | | | |
| C6− | 3.81 | 2.99 | 3.81 | 0.00 |
| Benzene | 12.56 | 17.27 | 20.48 | 26.26 |
| Toluene | 58.85 | 50.82 | 44.18 | 41.47 |
| Ethylbenzene | 0.53 | 0.89 | 1.27 | 0.00 |
| Xylenes | 18.59 | 21.60 | 22.61 | 27.10 |
| C9 Aromatics | 3.52 | 4.17 | 5.18 | 5.21 |
| C10+ Aromatics | 2.14 | 2.24 | 2.46 | 0.00 |
| Total | 100.00 | 100.00 | 100.00 | 100.00 |
| Conversion-wt % | | | | |
| Toluene | 40.29 | 48.44 | 55.17 | 58.52 |
| Approach To Equil., % | | | | |
| Xylenes | 68.6 | 79.7 | 83.4 | 100.0 |
| Benzene | 47.8 | 65.8 | 78.0 | 100.0 |
| C8 Aromatics Distribution-% | | | | |
| EB | 2.78 | 3.97 | 5.33 | |
| Xylenes | 97.22 | 96.03 | 94.67 | |

[1]Equilibrium product distribution at 620° F.

Comparative Example 15—Testing of SSZ-25

SSZ-25 was prepared as described in WO 96/29284, Ex. 17. It was tested in the same way that Al-SSZ-33 and SSZ-35 were tested, as described in Example 6. Synthetic feed 5A-1 was used. The results with SSZ-25 are shown in the Table below and in FIGS. 1 and 2. As shown in FIG. 1, SSZ-25 is less active than Al-SSZ-33 and SSZ-35 from a toluene conversion standpoint. In addition, as shown in FIG. 2, the catalyst has a lower XATE and therefore is less selective to xylenes than Al-SSZ-33 and 35.

| SSZ-25 | 15-1 | 15-2 | 15-3 | 15-4 | 15-5 | 15-6 |
|---|---|---|---|---|---|---|
| Hr on Stream | 4.9 | 23.2 | 25.8 | 30.5 | 53.5 | 59.2 |
| Temperature, °F. | 550 | 600 | 650 | 750 | 800 | 850 |
| Component, wt % | | | | | | |
| C6− | 0.14 | 0.11 | 0.17 | 0.54 | 1.03 | 2.10 |
| Benzene | 1.76 | 1.50 | 2.28 | 6.29 | 8.23 | 11.36 |
| Toluene | 67.94 | 62.98 | 57.17 | 55.74 | 48.50 | 41.89 |
| Ethylbenzene | 0.00 | 0.00 | 0.00 | 0.05 | 0.08 | 0.15 |
| Xylenes | 2.68 | 2.48 | 4.99 | 15.58 | 20.85 | 27.91 |
| 135 TMBZ | 7.93 | 9.02 | 9.37 | 5.79 | 5.33 | 3.99 |
| 124 TMBZ | 17.29 | 20.90 | 22.30 | 13.39 | 12.86 | 9.74 |
| 123 TMBZ | 1.96 | 2.66 | 3.04 | 1.78 | 1.86 | 1.40 |
| MEBZ | 0.13 | 0.11 | 0.17 | 0.18 | 0.21 | 0.24 |
| C10+ Aromatics | 0.16 | 0.21 | 0.51 | 0.65 | 1.06 | 1.24 |
| Total | 100.00 | 100.00 | 100.00 | 100.00 | 100.00 | 100.00 |
| Total TMBZ | 27.19 | 32.57 | 34.71 | 20.97 | 20.05 | 15.13 |
| Conversion-wt % | | | | | | |
| Toluene | (17.41) | (8.84) | 1.21 | 3.68 | 16.19 | 27.62 |
| TMBZ | 34.90 | 22.00 | 16.89 | 49.79 | 51.99 | 63.78 |
| Approach to Equil., % | | | | | | |
| Xylene | 6.4 | 6.0 | 120 | 37.5 | 50.1 | 67.1 |
| Benzene | 27.4 | 23.4 | 35.5 | 98.0 | 128.2 | 176.9 |

Example 16—Brief Discussion of Figures Comparing Zeolites Performance

FIG. 1: This Figure shows how toluene conversion varies as a function of temperature for SSZ-25, Al-SSZ-33, SSZ-35, beta zeolite and mordenite using synthetic feed 5A. The equilibrium toluene conversion at 620° F. is also shown for comparison. This value is 55.33 wt %. Both Al-SSZ-33 and SSZ-35 were found to be much more active than the other catalysts, requiring a lower temperature to achieve a given toluene conversion. At 600° F., both Al-SSZ-33 and SSZ-35 have toluene conversions of 50.3 and 49.4 wt % respectively compared to no more than 10–15 wt % for the other three catalysts. The maximum conversion for beta zeolite was about 28.2 wt % at 750° F. Mordenite attained 9.6 wt % at 800° F.

FIG. 2: This Figure compares the xylene selectivity of two catalysts of the invention—Al-SSZ-33 and SSZ-35—to SSZ-25, beta zeolite and mordenite, as a function of temperature. The xylene selectivity is defined by the Xylene Approach To Equilibrium (XATE) expressed as a percentage and is the ratio of the actual xylene yield to the theoretical xylene yield at equilibrium when the feed consists of toluene and TMBZ, i.e., using synthetic feeds 5A-1 and 5A-2. Both Al-SSZ-33 and SSZ-35 have the highest XATE. In the case of SSZ-35, the XATE reaches a maximum value of 90.1% at 650° F. compared to 83.7% at 750° F. for beta zeolite.

FIG. 3: This Figure is similar to FIG. 1 except that the feed used was the Commercial C9+ aromatics feed combined with toluene (Feed 5B). The catalysts compared are Ni/SSZ-35 and Ni/beta zeolite. As can be seen, Ni/SSZ-35 is more active than Ni/beta zeolite. Higher toluene conversions are reached at lower temperatures with the catalyst of the invention than with beta zeolite.

While the invention has been described above in terms of preferred embodiments, it is to be understood that variations and modifications may be used as will be appreciated by those skilled in the art. Indeed, there are many variations and modifications to the above embodiments which will be readily evident to those skilled in the art, and which are to be considered within the scope of the invention as defined by the following claims.

What is claimed is:

1. A gas phase aromatics transalkylation process, comprising
   contacting a stream comprising one or more aromatic hydrocarbons, at least one of said aromatic hydrocarbons having at least one alkyl group attached thereto, said alkyl group selected from the group consisting of C1, C2, C3 and C4 hydrocarbyl groups,
   with a catalyst comprising a zeolite selected from the group consisting of SSZ-26, Al-SSZ-33, CIT-1, SSZ-35, and SSZ-44,
   in the presence of added hydrogen and in the gas phase, to produce transalkylated product.

2. The gas phase aromatics transalkylation process of claim 1 wherein the aromatic hydrocarbon stream comprises one or more hydrocarbons selected from the group consisting of benzene, toluene, xylene, 1,2,3, trimethylbenzene, 1,2,4, trimethylbenzene, 1,3,5, trimethylbenzene, ethylbenzene, diethylbenzene, isopropylbenzene and diisopropylbenzene.

3. The gas phase aromatics transalkylation process of claim 2 wherein the aromatic hydrocarbon stream comprises toluene and trimethylbenzene.

4. The gas phase aromatics transalkylation process of claim 1 or 3 wherein the zeolite is selected from the group consisting of Al-SSZ-33 and SSZ-35.

5. The gas phase aromatics transalkylation process of claim 3 wherein the feed comprises a mixture of three trimethylbenzenes.

6. The process of claim 5, wherein said mixture of trimethylbenzenes is at least 10 wt % of a C9+ aromatics stream.

7. The gas phase aromatics transalkylation process of claims 1 or 3 wherein the zeolite contains a mild hydrogenation metal.

8. The process of claim 7 wherein the metal is selected from the group consisting of palladium and nickel.

9. The process of claim 8 wherein the metal is nickel.

10. The gas phase aromatics transalkylation process of claim 3 wherein the process produces an effluent having a xylene to benzene weight ratio greater than 5, and an approach to xylene equilibrium that is at least 80%, when tested using a synthetic test feed comprising about 60 wt % toluene and about 40 wt % trimethylbenzene.

11. The gas phase aromatics transalkylation process of claims 1 or 3 wherein the mole ratio of hydrogen to aromatic hydrocarbons is between 2:1 and 5:1.

12. The gas phase aromatics transalkylation process of claims 1 or 3 wherein the temperature is between about 550° F. and about 800° F. and the pressure is between 200 and 400 psig.

13. The gas phase aromatics transalkylation process of claim 3 wherein the transalkylated product contains a mixture of xylenes that are at or near equilibrium, and also contains less than 4 wt % ethylbenzene.

14. The gas phase aromatics transalkylation process of claim 2 wherein the transalkylation process is toluene disproportionation.

15. The gas phase aromatics transalkylation process of claim 14, wherein the zeolite further comprises a mild hydrogenation metal.

16. The gas phase aromatics transalkylation process of claim 15, wherein the mild hydrogenation metal is selected from the group consisting of palladium and nickel.

17. The gas phase aromatics transalkylation process of claim 2 wherein the aromatic hydrocarbons comprise benzene and trimethylbenzene.

18. The gas phase aromatics transalkylation process of claim 17, wherein the zeolite further comprises a mild hydrogenation metal.

19. The gas phase aromatics transalkylation process of claim 18, wherein the mild hydrogenation metal is selected from the group consisting of palladium and nickel.

20. A gas phase aromatics transalkylation process for preparing xylenes, comprising
   a) separating a whole naphtha into streams including a light naphtha comprising C7 hydrocarbons and a heavy naphtha comprising C9 hydrocarbons;
   b) reforming the light naphtha using a Pt L-zeolite catalyst, to produce a reformate containing toluene;
   c) separating a toluene-rich stream from said first reformate;
   d) reforming the heavy naphtha using a non-zeolitic Group VIII reforming catalyst, to produce a second reformate containing trimethylbenzene;
   e) separating a stream containing trimethylbenzene from said second reformate;
   f) transalkylating said toluene-rich stream with said stream containing trimethylbenzene in the gas phase in the presence of added hydrogen using a catalyst comprising a zeolite selected from the group consisting of SSZ-26, Al-SSZ-33, CIT-1, SSZ-35, and SSZ-44; and
   g) separating a xylene-rich stream from the transalkylation reaction effluent of step f).

21. The process of claim 20 wherein the zeolite is selected from the group consisting of Al-SSZ-33 and SSZ-35.

22. The process of claim 20, wherein the zeolite further comprises a mild hydrogenation metal.

23. The process of claim 20, wherein the mild hydrogenation metal is selected from the group consisting of palladium and nickel.

* * * * *